United States Patent [19]

Suginaka et al.

[11] Patent Number: 5,654,171
[45] Date of Patent: Aug. 5, 1997

[54] POLYPEPTIDE, PROCESS FOR PREPARING THE SAME AND PHARMACEUTICAL COMPOSITIONS AND COSMETICS CONTAINING THE POLYPEPTIDE

[75] Inventors: Hidekazu Suginaka; Motoyuki Sugai, both of Hiroshima; Yonman Hon, Naruto; Hideo Ogai, Hyogo, all of Japan

[73] Assignee: Earth Chemical Company, Ltd., Hyogo, Japan

[21] Appl. No.: 353,341

[22] Filed: Dec. 5, 1994

Related U.S. Application Data

[63] Continuation of Ser. No. 145,711, Sep. 8, 1993, abandoned, which is a continuation of Ser. No. 689,252, Jun. 12, 1991, abandoned.

Foreign Application Priority Data

Sep. 5, 1989 [JP] Japan .................................. 1-230703

[51] Int. Cl.$^6$ .............................. A61K 7/00; A61K 38/16; C07K 14/31; C12N 15/31
[52] U.S. Cl. .................. 435/69.1; 435/252.3; 435/320.1; 514/12; 514/844; 514/969; 530/350; 536/23.7
[58] Field of Search .................. 435/69.1, 320.1, 435/252.3, 252.31, 252.33; 514/2, 12, 844, 969; 530/350, 825, 820; 536/23.7

[56] References Cited

PUBLICATIONS

Sugai, M. et al. *Cell.Struct.Funct.* 12(4):395–400 (1987).
Sugai, M. *Hiroshima Daigaku Shigaku Zasshi* 19(2):391–401.
Inoue, S. Biochem. Biophys. Res. Comm. 174:459–464. (1991).
Lee, C.C. et al. *Science* 239:1288–1291 (1988).

*Primary Examiner*—Dian C. Jacobson
*Attorney, Agent, or Firm*—Larson & Taylor

[57] ABSTRACT

The present invention relates to a polypeptide (CIF Cornifation Inhibiting factor) characterized in that the polypeptide has a sequence of 212 amino acid residues represented by the formula (1) and a molecular weight of about 24000 daltons as determined by SDS-PAGE, a process for preparing the polypeptide, pharmaceutical compositions and cosmetics comprising the polypeptide, and a method of preventing or curing symptoms of skin diseases due to abnormal cornification of the skin with use of the polypeptide.

16 Claims, 3 Drawing Sheets

POLYPEPTIDE, PROCESS FOR PREPARING THE SAME AND PHARMACEUTICAL COMPOSITIONS AND COSMETICS CONTAINING THE POLYPEPTIDE

This application is a continuation of application Ser. No. 08/145,711 filed Sep. 8, 1993, now abandoned, which in turn is a continuation of U.S. Ser. No. 689,252, filed Jun. 12, 1991, now abandoned.

FIELD OF INDUSTRIAL APPLICATION

The present invention relates to a novel polypeptide, a process for preparing the same, pharmaceutical compositions and cosmetics containing the polypeptide, and a method of curing skin diseases with use of the polypeptide.

DISCLOSURE OF THE INVENTION

*Staphylococcus aureus* has strong pathogenicity as suggested by the fact that it had been previously named as Micrococcus pyogenes and is one of clinically important pathogens causing various suppurative diseases and the like even at the present time when various antibiotics have been developed. The skin infections caused by *Staphylococcus aureus* are predominantly suppurative diseases, which result in lesions generally exhibiting, in addition to the so-called four distinct symptoms of inflammation, mingled forms of symptoms on the skin inclusive of characteristic ones, such as desquamation, erosion and blisters. It is understood that such versatile cutaneous lesions are due to various pathogenic factors produced by *Staphylococcus aureus*. However, One strain of *Staphylococcus aureus* produces more than thirty kinds of extracellular products, and one extracellular product has a wide variety of biologically activities (Wadstrom, T., Ann. N.Y. Acad. Sci., 236, 343 (1974); Rogolsky, M., Microbiol. Rev., 43, 320 (1979)). This presents serious difficulties in clarifying the role of extracellular products in staphylococcal infections. Up to date, therefore, almost all the extracellular products have yet to be clarified as to the relation thereof to the skin lesions and of course have not been isolated or purified.

It is thought that the infection of the skin with *Staphylococcus aureus* occurs through the process of adhesion of the staphylococci to the skin, penetration thereof into the skin and pathogenesis involving proliferation. Accordingly, the staphylococci first attacks the epidermis. The epidermis is composed of several layers of cells including the stratum corneum as the outermost layer through the stratum basale, and these cells are in the course of a series of differentiation steps. Once injured epidermis is infected with *Staphylococcus aureus*, the bacteria presumably produces some pathogenic factors which disturb formation of the epidermal structure or impairs the physiological function of the epidermis, consequently giving rise to various symptoms described above.

The extracellular products of *Staphylococcus aureus* the activity of which has already been clarified are limited solely to an enterotoxin, hemolysin (hemolysis leukocidin) and exfoliative toxin (ET) (John J. Iandolo, Am. Rev. Microbiol., 43, 375 (1989)). The above-mentioned enterotoxin, hemolysin and exfoliative toxin respectively have activity to cause vomiting, diarrhea, etc., activity to cause hemolysis of erythrocyte, granulocytes, etc., and activity to cause epidermolysis in neonatal mice when intracutaneously given thereto.

We have studied effects of extracellular products of *Staphylococcus aureus* on the cornification of epidermal cells. Using the epidermal cells of mice cultured by the method of Yuspa et al. (Cell, 19, 245 (1980)), we found that the extracellular products of a *Staphylococcus aureus* strain separated from lesions of the skin contain an active factor which inhibits the cornification of such epidermal cells in vitro, and succeeded in isolating the active factor. During the subsequent research, we have identified the amino acid sequence of the active factor and the DNA sequence coding for the factor, prepared a gene containing the DNA sequence, a vector containing the same and a microorganism transformed with the vector, and established a process for preparing the polypeptide by the gene engineering techniques of culturing the transformed microorganism. Thus, the present invention has been accomplished.

The present invention provides a polypeptide (CIF: cornification inhibiting factor) characterized in that the polypeptide has a sequence of 212 amino acids represented by the following formula (1) and a molecular weight of about 24000 daltons as determined by SDS-PAGE. Formula (1) (SEQ ID NO. 1):

| 1 | | | | | | | | | 10 |
|---|---|---|---|---|---|---|---|---|---|
| Ala | Asp | Val | Lys | Asn | Phe | Thr | Asp | Leu | Asp |
| 11 | | | | | | | | | 20 |
| Glu | Ala | Thr | Lys | Trp | Gly | Asn | Lys | Leu | Ile |
| 21 | | | | | | | | | 30 |
| Lys | Gln | Ala | Lys | Tyr | Ser | Ser | Asp | Asp | Lys |
| 31 | | | | | | | | | 40 |
| Ile | Ala | Leu | Tyr | Glu | Tyr | Thr | Lys | Asp | Ser |
| 41 | | | | | | | | | 50 |
| Ser | Lys | Ile | Asn | Gly | Pro | Leu | Arg | Leu | Ala |
| 51 | | | | | | | | | 60 |
| Gly | Gly | Asp | Ile | Asn | Lys | Leu | Asp | Ser | Thr |
| 61 | | | | | | | | | 70 |
| Thr | Gln | Asp | Lys | Val | Arg | Arg | Leu | Asp | Ser |
| 71 | | | | | | | | | 80 |
| Ser | Ile | Ser | Lys | Ser | Thr | Thr | Pro | Glu | Ser |
| 81 | | | | | | | | | 90 |
| Val | Tyr | Val | Tyr | Arg | Leu | Leu | Asn | Leu | Asp |
| 91 | | | | | | | | | 100 |
| Tyr | Leu | Thr | Ser | Ile | Val | Gly | Phe | Thr | Asn |
| 101 | | | | | | | | | 110 |
| Glu | Asp | Leu | Tyr | Lys | Leu | Gln | Gln | Thr | Asn |
| 111 | | | | | | | | | 120 |
| Asn | Gly | Gln | Tyr | Asp | Glu | Asn | Leu | Val | Arg |
| 121 | | | | | | | | | 130 |
| Lys | Leu | Asn | Asn | Val | Met | Asn | Ser | Arg | Ile |
| 131 | | | | | | | | | 140 |
| Tyr | Arg | Glu | Asp | Gly | Tyr | Ser | Ser | Thr | Gln |
| 141 | | | | | | | | | 150 |
| Leu | Val | Ser | Gly | Ala | Ala | Val | Gly | Gly | Arg |
| 151 | | | | | | | | | 160 |
| Pro | Ile | Glu | Leu | Arg | Leu | Glu | Leu | Pro | Lys |
| 161 | | | | | | | | | 170 |
| Gly | Thr | Lys | Ala | Ala | Tyr | Leu | Asn | Ser | Lys |
| 171 | | | | | | | | | 180 |
| Asp | Leu | Thr | Ala | Tyr | Tyr | Gly | Gln | Gln | Glu |
| 181 | | | | | | | | | 190 |
| Val | Leu | Leu | Pro | Arg | Gly | Thr | Glu | Tyr | Ala |
| 191 | | | | | | | | | 200 |
| Val | Gly | Ser | Val | Glu | Leu | Ser | Asn | Asp | Lys |
| 201 | | | | | | | | | 210 |
| Lys | Lys | Ile | Ile | Ile | Thr | Ala | Ile | Val | Phe |
| 211 | 212 | | | | | | | | |
| Lys | Lys | | | | | | | | |

The amino acid residues of peptides are herein represented by symbols according to the amino acid nomenclature adopted by IUPAC or by symbols generally used in the art. The nucleotide sequences of nucleic acids are also expressed similarly.

The physiological activity of the polypeptide (CIF) of the present invention, i.e., the activity thereof to inhibit the cornification of epidermal cells, is determined by the method to be described in one of the examples given later.

The CIF of the invention is specified in that it has the above-mentioned amino acid sequence and molecular weight.

The CIF of the invention includes not only the CIF (natural type) derived from *Staphylococcus aureus* but also the CIF (synthetic type) prepared by gene engineering techniques.

The CIF of the invention is definitely distinguished from the ET mentioned by the amino acid composition and amino acid sequence thereof. Moreover, the CIF of the invention does not have the activity to cause epidermolysis in neonatal mice when intracutaneously given thereto.

The CIF of the present invention is specified also by the fact that it has the following physical and chemical properties.

1) Single protein

A 6-μg quantity of the CIF of the invention is dissolved in 0.05% trifluoroacetic acid (TFA), and the solution is applied to a Protein $C_4$ (product of The Sep/a/ra/tions Group) column previously equilibrated with 0.05% TFA containing 10% acetonitrile, followed by linear gradient elution with up to 60% acetonitrile. Consequently a single peak is obtained, indicating activity.

SDS-PAGE reveals that the CIF of the invention exhibits the same electrophoretic profile regardless of whether the reducing agent of β-mercaptoethanol is present, and a single band appears when the gel is stained with Coomassie Brilliant Blue (CBB). Thus, the CIF is identified as a single protein.

2) Isoelectric point determined by chromatofocusing

By chromatofocusing using a PBE94 column (Pharmacia LKB Biotechnology AB) in the range of pH 6.0–9.0, the present substance is eluted at about pH 8.2. Thus, the substance is identified as a basic protein (pI8.2).

3) pH stability and thermal stability

The CIF of the invention is stable in the range of pH 2–10. The factor is completely inactivated when heat-treated at 60° C. for 30 minutes.

The CIF of the present invention can be identified and quantitatively determined by immunoassay methods, which include, for example, the fluorescent antibody method, radioimmunoassay, enzyme-linked immunosorbent assay (ELISA), etc. Among these, ELISA is desirable because this method is easy to practice. Specifically stated, ELISA is conducted by the following procedure. Each of the wells of a microplate is coated with anti-CIF IgG, which is then reacted with a test sample diluted with PBS containing 0.1% BSA. Then enzyme-labeled antibodies are added to the well to react with CIF bound to the coated anti-CIF IgG, followed by a further reaction with addition of 0.25% o-phenylenediamine and 0.15% aqueous solution of hydrogen peroxide. Subsequently, 1N sulfuric acid is added to the reaction mixture, and the absorbance of the mixture is measured at 492 nm.

The above procedures will be described in detail in one of the examples to follow.

The CIF of the present invention is useful for elucidating the physiological function of epidermal cells and the mechanism of infection with the bacteria in view of the fact that the factor has unique activity to inhibit the cornification of epidermal cells. The factor can be used in pharmaceuticals for curing various skin—infections, such as tylosis palmaris et plantaris and ichthyosis which are diseases associated with abnormal cornification (differentiation-proliferation), and also in cosmetics for softening the skin.

A detailed description of a process for preparing the CIF of the present invention will be given below.

The natural CIF of the invention can be obtained, for example, by culturing a staphylococcus separated from the skin of patients having a staphylococcal scalded skin syndrome (SSSS). Typical of such an origin microorganism is, for example, *Staphylococcus aureus* E-1 strain. This strain is one separated from the skin of a one-year-old male infant who was diagnosed as SSSS at Hiroshima Prefectural Hospital, Internal Department, identified as such and provided by Dr. Kuwahara of the internal department. The strain is not eligible for deposition in Fermentation Research Institute and is preserved by us in condition for distribution.

The original microorganism can be cultured by various methods in the same manner as usual microorganisms of like type, for example, by subculture on a Trypticasesoy Broth (Becton Dickinson and Co., MD, U.S.A.) slant medium.

The proliferation is conducted by culture, for example, in TY medium (10 g/liter of yeast extract, 17 g/liter of Trypticase, 5 g/liter of NaCl and 2.5 g/liter of $K_2HPO_4$ at 37° C. for 24 hours while being allowed to stand, and thereafter conducted by culture in the presence of 10% $CO_2$ at 37° C. for 24 hours with shaking.

The resulting culture solution is subjected to centrifugation, membrane filtration or like procedure in the usual manner, whereby a culture supernatant containing the desired CIF can be separated off.

A crude product containing the CIF can be prepared from the culture supernatant thus obtained by a suitable combination of known procedures. Examples of such procedures are salting-out with ammonium sulfate or like treatment using a protein precipitant, centrifugation, dialysis, ultrafiltration, concentration, etc.

The crude product can be purified also by known method, such as gel filtration, liquid chromatography, electrophoresis, affinity chromatography, chromatofocusing, reverse-phase high performance liquid chromatography, ion exchange column chromatography and a combination of such methods. More specifically, examples of useful methods are cation exchange column chromatography with TSK Gel SP-Toyopearl 650M (product of Tosoh Corporation) or the like, hydroxyapatite chromatography with HA-1000 (product of Tosoh Corporation) or the like, and reverse-phase high performance liquid chromatography with Protein $C_4$ (product of the Sep/a/ra/tions Group). Also useful is SDS-PAGE according to the method of Laemmli (Laemmli, U.K., Nature, 227, 680 (1970)), etc.

In this way, the CIF (natural type) of the present invention can be isolated which comprises a protein i.e., polypeptide of the formula (1).

While the CIF of the present invention can be prepared by culturing the strain *Staphylococcus aureus* E-1, followed by separation and purification, the factor can be prepared also by gene engineering techniques.

More specifically, the CIF (synthetic type) of the invention can be prepared by utilizing a gene including a sequence coding for the CIF, i.e., by introducing the gene into a vector of microorganism, and causing the microorganism to replicate, transcribe and translate the gene in its cells. This method is amenable to quantity production, is therefore especially advantageous and is one of the objects of the invention.

The gene for use in preparing the CIF by gene engineering techniques is characterized in that it contains a nucleotide sequence coding for the CIF. The invention also provides this novel CIF gene.

We have determined the amino acid sequence of a precursor of the CIF by analyzing a genes for the natural CIF. The amino acid sequence of the CIF precursor is represented by the formula (2) below, The present invention provides CIF genes which include a DNA sequence coding for the amino acid sequence of the CIF precursor, in addition to a DNA sequence coding for the amino acid sequence of CIF represented by the formula (1). The nucleotide sequence of the formula (2) shows an example of such DNA sequence along with the corresponding amino acid sequence, whereas the CIF gene of the invention is not limited to this example. Formula (2) (SEQ ID NO. 2 and 4):

```
A A A A A C A G A A T A A A T A T T T T C T T T T A A T A A T A A A A T A T C A       40
                   S s p I
T A T A A T G A A A T T A T A T A T A A A T A A C A A T C A A G A G G A G A T T T T T   83

ATG AAA AAC AAA TTA CTT TTT AAA ATT TTT                                               113
Met Lys Asn Lys Leu Leu Phe Lys Ile Phe
-35                                 -26

TTG AGT TTA TCT TTA GCA TTA AGC GTT TAT                                               143
Leu Ser Leu Ser Leu Ala Leu Ser Val Tyr
-25                                 -16

TCA ATT AAT GAT AAA ATC ATA GAA GTA TCT                                               173
Ser Ile Asn Asp Lys Ile Ile Glu Val Ser
-15                                 -6

AAT ACT TCT TTA GCA GCT GAT GTT AAA AAT                                               203
Asn Thr Ser Leu Ala Ala Asp Val Lys Asn
-5          -1  1                   5

TTC ACT GAT TTA GAT GAG GCA ACT AAA TGG                                               233
Phe Thr Asp Leu Asp Glu Ala Thr Lys Trp
6                                   15

GGG AAT AAA CTT ATA AAA CAA GCT AAG TAT                                               263
Gly Asn Lys Leu Ile Lys Gln Ala Lys Tyr
16                                  25

AGT TCG GAT GAT AAA ATA GCT CTA TAC GAA                                               293
Ser Ser Asp Asp Lys Ile Ala Leu Tyr Glu
26                                  35

TAT ACA AAA GAT AGT TCT AAG ATA AAT GGT                                               323
Tyr Thr Lys Asp Ser Ser Lys Ile Asn Gly
36                                  45

CCA TTA AGA CTC GCA GGT GGA GAT ATT AAT                                               353
Pro Leu Arg Leu Ala Gly Gly Asp Ile Asn
46                                  55

AAG CTA GAT TCA ACA ACT CAA GAC AAA GTA                                               383
Lys Leu Asp Ser Thr Thr Gln Asp Lys Val
56                                  65

AGA AGA TTA GAT TCA TCT ATT TCT AAA TCT                                               413
Arg Arg Leu Asp Ser Ser Ile Ser Lys Ser
66                                  75

ACT ACT CCT GAA TCT GTA TAC GTT TAT AGA                                               443
Thr Thr Pro Glu Ser Val Tyr Val Tyr Arg
76                                  85

CTT TTA AAT TTA GAT TAT TTG ACA AGT ATC                                               473
Leu Leu Asn Leu Asp Tyr Leu Thr Ser Ile
86                                  95

GTT GGA TTT ACA AAT GAA GAT TTA TAT AAA                                               503
Val Gly Phe Thr Asn Glu Asp Leu Tyr Lys
96                                  105

TTA CAA CAG ACC AAT AAT GGC CAG TAT GAT                                               533
Leu Gln Gln Thr Asn Asn Gly Gln Tyr Asp
106                                 115

GAA AAT CTA GTT AGA AAG CTT AAT AAC GTT                                               563
Glu Asn Leu Val Arg Lys Leu Asn Asn Val
116                                 125

ATG AAT AGC AGA ATA TAT AGA GAA GAC GGA                                               593
Met Asn Ser Arg Ile Tyr Arg Glu Asp Gly
126                                 135

TAC TCT AGT ACA CAA TTA GTT AGT GGA GCA                                               623
Tyr Ser Ser Thr Gln Leu Val Ser Gly Ala
136                                 145
```

```
                                                        -continued
GCT GTA GGT GGT AGA CCT ATT GAA TTA AGG                  653
Ala Val Gly Gly Arg Pro Ile Glu Leu Arg
146                                 155

TTA GAA TTA CCA AAA GGG ACT AAA GCT GCG                  683
Leu Glu Leu Pro Lys Gly Thr Lys Ala Ala
156                                 165

TAT CTT AAT TCT AAA GAT TTA ACT GCT TAC                  713
Tyr Leu Asn Ser Lys Asp Leu Thr Ala Tyr
166                                 175

TAT GGT CAA CAA GAA GTT TTA TTA CCT AGA                  743
Tyr Gly Gln Gln Glu Val Leu Leu Pro Arg
176                                 185

GGC ACA GAA TAC GCT GTT GGA AGT GTA GAA                  773
Gly Thr Glu Tyr Ala Val Gly Ser Val Glu
186                                 195

TTG TCA AAT GAT AAA AAG AAA ATC ATA ATA                  803
Leu Ser Asn Asp Lys Lys Lys Ile Ile Ile
196                                 200

ACA GCT ATT GTT TTT AAA AAA TAG AAA TAT                  833
Thr Ala Ile Val Phe Lys Lys ***
206                 212

A A A C A A A G T A A T A A C A A G G A T T A A T A A A T T A A A A A T T T T    873
A A T T A A T A T T T T C T A T A A C T A A A A G A A                            900
     S sp I
```

The CIF gene of the present invention can be prepared, for example, from a CIF-producing staphylococcus strain as described below and also by various processes already known generally. Based on CIF and the gene information thereof herein disclosed, the gene can be prepared, for example, through the chemical synthesis of nucleic acid sequence by the phosphite triester method (Nature, 310, 105 (1984)) or the like, or by a combination of known processes.

Among processes for preparing the CIF gene of the present invention, a process for preparing the gene from CIF-producing staphylococcus strains will be described below in greater detail.

The gene can be obtained from CIF-producing staphylococcus strains, typical of which is *Staphylococcus aureus* E-1 strain. The chromosomal DNA of the microorganism can be extracted by various usual methods. For example, cells are lysed with lysostaphin, and then treated with SDS, followed by treatment with phenol/chloroform and precipitation from ethanol, whereby the DNA can be obtained.

The screening of the CIF gene from the resulting DNA can be done by a combination of procedures already known, for example, by cleaving the DNA with commercial restriction endonucleases separating DNA bands by electrophoresis and screening the CIF gene by Southern blotting. For Southern blotting, the DNA fragments separated on a electrophoresis gel are transferred to a nitrocellulose membrane filter and reacted with a labeled probe, which selectively binds to the desired DNA sequence. Thus, this nature of the probe is utilized to obtain the desired gene by screening. The probe is a nucleic acid sequence complementary to the desired DNA sequence. A chemically synthesized DNA sequence is generally used as the probe and is advantageous to use. The DNA sequence of the probe can be determined based on the partial amino acid sequence of the CIF. The DNA fragment thus obtained contains the gene of the invention.

The CIF gene obtained by the above procedure can be cloned on a plasmid by a usual method. For example, a fragment containing the CIF gene cleaved with EcoRI and purified is inserted into the cleavage site of pBR328 (X. Soberon, L. Covarrubias and F. Bolivar, Gene, 9, 287 (1980)) similarly cleaved with EcoRi, whereby a desired recombinant vector can be obtained. Various methods generally used can be employed for introducing the recombinant vector into host cells, for the proliferation and individualization of the vector. For example, cells in the logarithmic growth phase are collected, treated with $CaCl_2$ or converted to protoplasts, and thereby made to easily accept the DNA before the introduction of the vector.

Conventional methods are usable for the foregoing procedures, for example, for the chemical synthesis of DNA fragments, enzymatic treatments for the cleavage, deletion, addition or ligation of DNA chains, and for the isolation, purification, replication and selection of DNA. More specifically, the DNA can be isolated and purified, for example, by agarose gel electrophoresis.

The DNA sequence of the gene of the invention to be obtained by the above process can be determined, for example, by the method of Sanger (Yanisch-Perron et al., Gene, 33, 103 (1985)), or the Maxam-Gilbert method (A. M. Maxam and W. Gilbert, Methods in Enzymology, 65, 499 (1980)). The DNA sequence can be easily determined also by using commercial sequencing kits or the like.

Thus, the DNA sequence containing the desired CIF gene and the corresponding amino acid sequence can be determined with reference to various pieces of literature (e.g., J. E. Darnell et al., "Molecular Cell Biology," Scientific American Books (1086)).

The formula (2) shows an example of DNA sequence containing the desired CIF gene thus determined, and of the corresponding amino acid sequence. Stated precisely, the formula shows the DNA sequence and amino acid sequence of a CIF precursor. Amino acid sequence of the CIF precursor includes a signal sequence, whose amino acid sequence can be determined, for example, by the method of Von Heijne (Nucl. Acids Res., 14, 4683 (1986)). According to the method, this DNA sequence codes for a CIF precursor having added thereto a signal sequence corresponding to the 35 amino acid residues (−35 to −1) at the N-terminal of the amino acid sequence of the CIF as represented by the formula (2). The mature CIF produced from the CIF precursor by the removal of the signal sequence comprises the amino acid sequence of the formula (1). This reveals that the CIF is a secretory protein which is generated by removal of the signal sequence from the primarily biosynthesized precursor.

Large quantities of CIF can be obtained utilizing the CIF gene of the present invention and resorting to gene recombination techniques. These techniques afford a recombinant DNA capable of expressing the gene in host cells. The recombinant DNA can be prepared by the usual method of the art and easily prepared based on the CIF gene information herein disclosed. Specific procedures for the preparation will be described in detail below.

Either eucaryotic cells or procaryotic cells can be used as host cells. The eucaryotic cells include cells of vertebrates, yeasts, etc. Generally useful as cells of vertebrates are, for example, COS cells (Y. Gluzman, Cell, 23, 175 (1981)), dihydrofolate reductase defective strain of Chinese hamster ovary cells (G. Urlaub and L. A. Chasin, Proc. Natl. Acad. Sci., U.S.A., 77, 4216 (1980)) and the like. However, useful cells are not limited to these examples. Useful expression vectors for vertebrate cells are those having a promoter positioned upstream of the gene to be expressed, RNA splicing sites, polyadenylation signal, transcription termination sequence, etc. These vectors may further have a replication origin when required. Examples of useful expression vectors include pSV2dhfr having SV40 early promoter (S. Subramani, R. Mulligan and P. Berg, Mol. Cell Biol., 1, 854 (1981)), which however is not limitative.

Yeasts are generally used as eucaryotic microorganisms, among which yeasts of the genus Saccharomyces are advantageously usable. Examples of preferred expression vectors for yeasts and like eucaryotic microorganisms include pAM82 having the promoter of acid phosphatase gene (A. Miyanohara et al., Proc. Natl. Acad. Sci., U.S.A., 80, 1 (1983)).

E. coli and Bacillus subtilis are generally used as hosts of procaryotic organisms. According to the present invention, for example, plasmid vectors can be used which are capable of replication in the host cells. To express the CIF gene in the vector, expression plasmids can be used which have a promoter and SD (Shine-Dalgarno) sequence upstream of the CIF gene, and a transcription termination sequence, etc. downstream of the CIF gene.

For example, E. coli K12 strain, etc. are widely used as hosts. As a vector for use in such hosts, pBR322 is generally used although not limitative. Thus, various known strains and vectors are usable. The promoters to be used include, for example, tryptophan promoter, PL promoter, lac promoter and lpp promoter etc. With use of any of these promoters, expression plasmids can be prepared which are capable of expressing the CIF gene. Competent E. coli cells prepared by treatment with $CaCl_2$ is transformed by the expression plasmid to obtain transformants, which is then cultured in the usual manner to obtain the CIF.

As another example of host, Bacillus subtilis Marburg 168 strain or the like is widely used. Generally serving as a vector for this host is pUB110 or a shuttle vector derived therefrom although not limitative. Various known strains and vectors are usable. Examples of promoters usable are α-amylase promoter, neutral protease promoter, SP02 promoter, etc. With use of any of these promoters, expression plasmids can be prepared which are capable of expressing the CIF gene. Bacillus subtilis, converted to protoplasts are transformed with the expression plasmid and the resulting desired transformant is cultured in the usual manner to obtain the CIF.

To obtain the CIF of the synthetic type having the same structure as natural CIF efficiently by gene recombination technology, the CIF is expressed as a fusion protein with a signal sequence, the protein is then translocated from inside the cell to the outside thereof or to the periplasm, and the CIF is thereafter obtained as a mature protein. More over, a plurality of CIF genes are introduced into an expression vector to effect simultaneous expression. Various other methods are also usable. Signal sequences usable for expressing the CIF as a fusion protein are signal sequence of various enzymes such as alkaline phosphatase, ampicillinase, α-amylase, β-glucanase, neutral protease and sphingomyelinase.

The CIF produced by the desired recombinant organisms intracellularly or extracellularly can be separated off in the usual manner, and isolated and purified by various procedures utilizing the physical or chemical properties of the CIF. Examples of such procedures are already described above.

In this way, the CIF (synthetic type) of the present invention can be prepared by gene engineering techniques.

The CIF of the present invention has activity to inhibit the cornification of epidermal cells. Accordingly, the CIF is effectively usable as a medicinal for preventing or curing skin diseases associated with abnormal cornification, such as tylosis palmaris et plantaris and ichthyosis, and as a cosmetic for softening the skin for beauty treatment.

The CIF of the present invention can be used in the form of an ointment, tincture, cream, solution, lotion, suspension or the like. Additives which are usually used in dermatology, such as oils, water, surfactants, moistening agents, alcohols, tackifiers, perfumes, antioxidants, chelating agents, pigments, preservatives, etc. can be suitably incorporated into the CIF-containing medicinals or cosmetics in such forms.

Surfactants, fats, preservatives, antioxidants and the like are added, for example, to creams. Examples of useful surfactants are nonionic surfactants such as polyoxyethylated aliphatic long-chain alcohols, glycerides thereof, sorbitol derivatives (Span, Tween, etc.) and mixtures of such compounds. Examples of useful fats are saturated semisolid or liquid hydrocarbons, saturated or unsaturated fatty acids and triglycerides thereof, long-chain aliphatic alcohols, vegetable or animal waxes, mixtures of such substances, etc. More specific examples are vaseline, caprylic acid, triglyceride thereof, caproic acid, triglyceride thereof, cetyl alcohol, stearyl alcohol, lanolin, paraffin, etc. Examples of useful preservatives are phenols, benzyl alcohol, γ-hydroxybenzoic acid and salts thereof, monothioglycerol, thimerosal, benzethonium chloride, chlorobutanol, sodium dehydroacetate, imidazolidinylurea and derivatives thereof, benzylalkyl ammonium chloride, p-chlorophenol, p-tert-butylphenol, cerium III nitrate, cetylalkyl ammonium chloride, cetyldiethylmethylammonium bromide, chlorothymol, cresols, sodium benzoate, etc. Examples of useful antioxidants are ascorbic acid, vitamin E, ascorbyl palmitate, butylhydroxyanisole, etc. Also usable are albumin, amino acids, inorganic salts, ionic surfactans and like protein stabilizers.

The dosage of the CIF differs with the form of preparation, age, body weight, etc. For parenteral administration, the CIF is usually given at a daily dose of 1 μg to 1 mg for adults, calculated as the amount of the effective component (polypeptide), once or dividedly several times.

EXAMPLES

Figure 1:
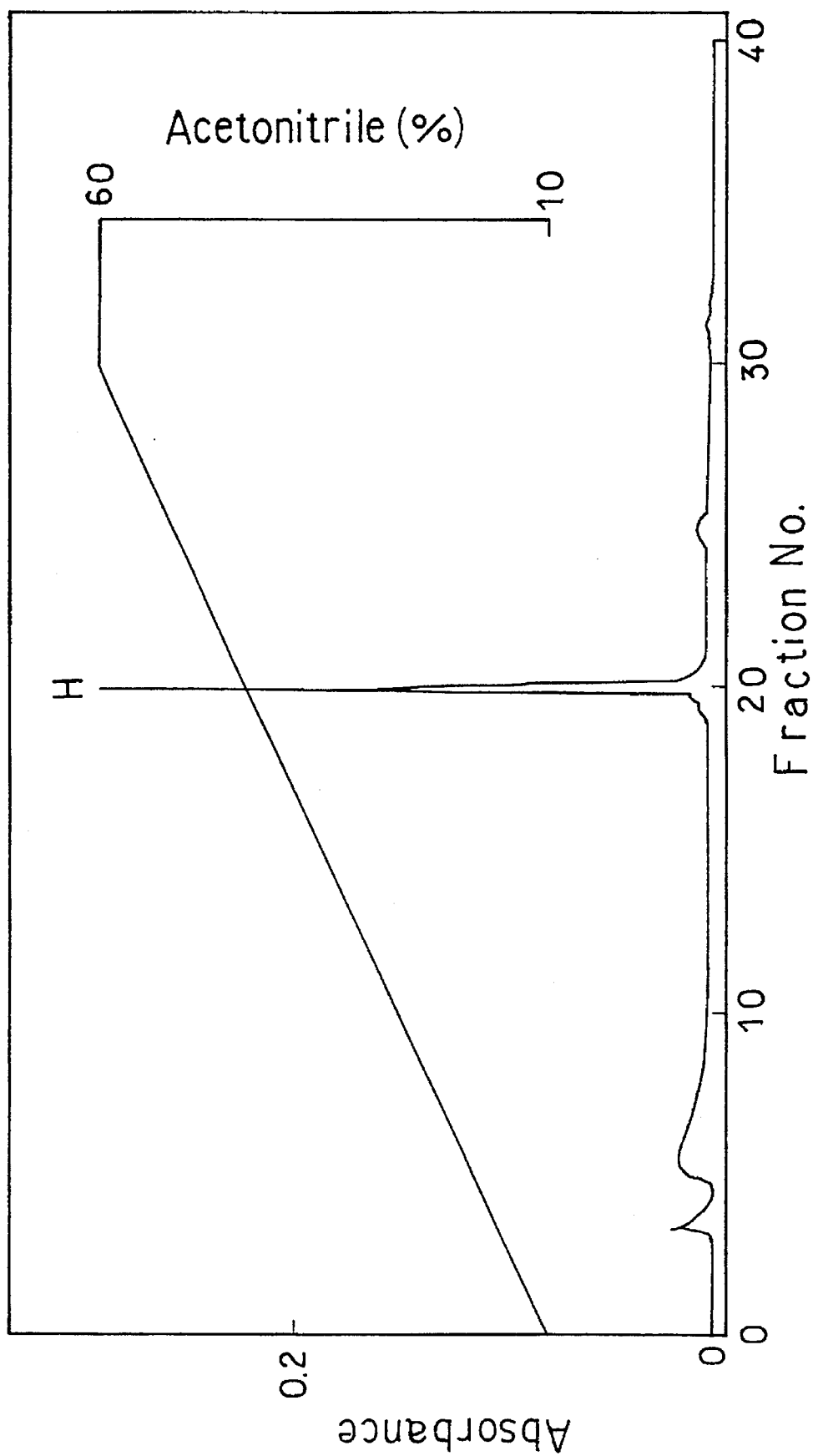
FIG. 1 shows the result of reverse-phase high performance liquid chromatography in CIF purification step (3), (iii) according to Example 1.

The present invention will be described below in greater detail with reference to examples. The physiological activity of CIF was determined and evaluated by the following method. [Determination of Activity to Inhibit Cornification of Epidermal Cells]

(1) Preparation of medium for culturing epidermal cells

To an Eagle's minimum essential medium (MEM, Joklik-modified) free from $Ca^{2+}$ were added 5 U/ml of penicillin G7 and 50 µg/ml of streptomycin (Grand Island Biological Co., N.Y., U.S.A). To the mixture was further added fetal calf serum (FCS) treated with Chelex-100 Resin (Bio Rad Lab., Richmond, CA, U.S.A.) to a concentration of 10%. The mixture was adjusted to a Ca concentration of 0.05 mM with 0.3M $CaCl_2$ solution, giving a low-concentration Ca medium (LCM).

Further a high-concentration Ca medium (HCM) adjusted to a Ca concentration of 1.0 mM was prepared in the same manner as above. The Ca concentration in the media was measured using an atomic absorption spectro photometer (Model 207, Hitachi Ltd.).

(2) Culture of epidermal cells

The back skin was collected from a neonatal CD-1 mouse, ICR strain and treated with 0.25% trypsin (Institute for Microbial Diseases) at 4° C. for 24 hours. The epidermis only was thereafter collected from the skin under a stereoscopicmicroscope (Model XTr, Olympus K.K.) and further treated with 0.25% trypsin at 37° C. for 1 hour to isolate epidermal cells. The number of living cells was determined by a dye exclusion test (Schrek, R., Arch. Pathol., 37, 319 (1944)) using Trypan Blue. A 35-mm plastic dish (Becton Dickinson and Co., U.S.A.) was inoculated with $1 \times 10^6$ cells/well, and also Cell Wells (24-well flat bottom, Corning, N.Y., U.S.A.) with about $3 \times 10^5$ cells/well, and the epidermal cells were cultured for 7 days in LCM in the presence of 5% $CO_2$ for use in experiments.

(3) Observation of morphological differentiation of epidermal cells

After the epidermal cells were cultured in LCM the medium was changed to HCM, and the resulting morphological changes were observed under an inverted microscope (Nikon MTD, product of Nippon Kogaku K.K.) with elapse of time for 48 hours.

(4) Quantitative determination of cornification of epidermal cells

The cornification of epidermal cells was quantitatively determined in the following manner according to the method of Peehl et al. (Peehl, D. M. and Ham, R. G., Growth and differentiation of human keratinocytes without a feeder or conditioned medium, In Vitro, 16, 516 (1980)).

The epidermal cells cultured in LCM were incubated in HCM for 48 hours and then treated with a mixture of 0.25% trypsin and 0.02% EDTA to obtain a cell suspension. A portion of the suspension was used to count the number of cells under a microscope (Nikon OPTIPHOT, product of Nippon Kogaku K.K.) using a hemocytometer, and the remainder of the cells was thereafter treated with 2% SDS-20 mM dithiothreitol at 90° C. for 10 minutes to extract insoluble cornified envelopes. The number of insoluble envelopes was counted with the hemocytometer, and the ratio thereof to all the cells was calculated to determine percent cornified cells.

(5) Detection and quantitative determination of activity to inhibit epidermal cornification When the medium was changed to HCM for the epidermal cells cultured in LCM using the 35-mm plastic dish, the sample to be tested was added to the cells, followed by the procedures (3) and (4) to detect and quantitatively determine the cornification inhibiting activity. When the medium was changed to HCM for the epidermal cells cultured in LCM, a simplified method of detecting the cornification inhibiting activity was also practiced by adding the sample to be tested, which was sequentially diluted by twofold, with phosphate-buffered saline (PBS) followed by the procedure (3).

EXAMPLE 1

(1) Culture of bacteria and preparation of culture supernatant

A loopful of *Staphylococcus aureus* E-1 subcultured on a Trypticase-soy Broth slant medium (Becton Dickinson and Co., MD, U.S.A.) was applied for inoculation to 30 ml of TY medium (10 g/liter of yeast extract, 17 g/liter of Trypticase, 5 g/liter of NaCl and 2.5 g/liter of $K_2HPO_4$), and cultured at 37° C. for 24 hours while being allowed to stand. The culture was then transferred to 3 liters of the same medium and cultured in the presence of 10% $CO_2$ at 37° C. for 24 hours with shaking. The resulting culture broth was centrifuged at 5000×g for 20 minutes, and the supernatant obtained was filtrated through a filter with a pore size of 0.22 µm (Millipore Co., Mass., U.S.A.) to prepare a sample of culture supernatant.

(2) Preparation of crude sample by salting-out with ammonium sulfate and concentration Solid ammonium sulfate was added to the supernatant sample obtained by the procedure (1) to 75% saturation. The mixture was allowed to stand at 4° C. for 24 hours and then centrifuged at 10000×g for 30 minutes to obtain a precipitate. The precipitate was dialyzed against 50 mM phosphate buffer (pH 7.0) and concentrated about fiftyfold as a concentrated culture filtrate (CCF).

The crude sample was checked for activity to inhibit cornification of epidermal cells. The epidermal cells cultured in LCM appeared like a beautiful arrangement of paving stone which is characteristic of epithelial cells, were individually small and relatively uniform and had distinct intercellular spaces. When the medium was changed to HCM to induce differentiation, the cells morphologically changed markedly. More specifically, the cells gradually expanded, forming desmosomes therebetween. The cells soon underwent vertical stratification, and about 24 hours after the induction of differentiation, cells having a horny membrane (cornified cells) started to increase in number. Forty eight hours after the induction of differentiation, the cells greatly increased in size individually, and numerous cornified cells were found.

When the medium was changed to HCM for inducing differentiation, the morphological differentiation to be induced by Ca was completely inhibited if the medium had added thereto a suitable amount (2.5 to 20 µg protein/ml) of the crude sample prepared from the fraction salted-out with ammonium sulfate. More specifically, the individual cells became slightly larger than the control, but distinct intercellular spaces were found. Further almost no cornified cells appeared.

When the resulting cells were further cultured in HCM free from the crude sample, the cells individually differentiated as in the first case wherein no crude sample was added to the medium. When the cells cultured for 48 hours in HCM with or without the crude sample added thereto were cultured in LCM free from the crude sample, the cells cultured in the absence of the crude sample no longer resumed the appearance of an arrangement of paving stones, failing to restore the proliferating ability. Nevertheless, the cells cultured in the presence of the crude sample started to change morphologically several minutes after the medium was changed to LCM and resumed the original arrangement of paving stones two hours later. Dividing cells were found 24 hours later.

The above findings indicated that the inhibition of cornification by the crude sample is reversible.

Next to quantitatively determine the cornification inhibiting activity, percent cornified cells was calculated according to "Determination of Activity to Inhibit Cornification of Epidermal Cells," (4) to find that in this percentage the cells cultured in the presence of the crude sample were exceedingly lower than those cultured otherwise, and were comparable with the epidermal cells cultured in LCM.

(3) Purification by chromatography

Solid ammonium sulfate was added to 75% saturation to the supernatant sample prepared in the same manner as the procedure (1). The mixture was allowed to stand at 4° C. for 24 hours and then centrifuged at 10000×g for 30 minutes to obtain a precipitate. The precipitate was dialyzed against 50 mM phosphate buffer (pH 7.0) to obtain a concentrated culture filtrate (CCF), which was subjected to following chromatography steps.

The quantitative protein determination in each step was conducted by the dye fixation method (Bio Rad Lab., Bradford, M.M., Anal. Biochem., 72, 249 (1976)) using bovine serum albumin (BSA) as a standard.

(i) The concentrated culture filtrate (CCF), used as the starting material, was first dialyzed against 50 mM phosphate buffer (pH 5.0), the dialyzate was applied to a TSK Gel SP-TOYOPEARL 650M column (product of Tosoh Corporation, flow rate 4 ml/min) equilibrated with the same buffer, and the nonadsorbed fraction was washed away with the same buffer in a volume several times the column volume. The activity was found to be adsorbed to the column, while no activity was in the run through fraction. Subsequently, linear gradient elution was conducted with 50 mM phosphate buffer (pH 5.0) to 50 mM phosphate buffer +0.5M NaCl (pH 5.0). Active fractions eluted approximately at 220–300 mM NaCl were pooled.

(ii) The pooled active fractions were dialyzed against 50 mM phosphate buffer (pH 6.9), and the dialyzate was applied to a HA-1000 column (product of Tosoh Corporation, flow rate 1 ml/min) equilibrated with the same buffer. The nonadsorbed fraction was washed away with the same buffer in a volume several times the column volumn, followed by linear gradient elution with up to 0.5M phosphate buffer (pH 6.9). Active fractions eluted at about 0.35M were pooled.

(iii) The pooled active fractions were adjusted to pH 5.0 with trifluoroacetic acid (TFA), then applied to Protein $C_4$ column (product of The Sep/a/ra/tions Group, flow rate 1 ml/min) which was equilibrated with 0.05% TFA solution containing 10% acetonitrile, and thereafter subjected to linear gradient elution with up to 60% acetonitrile. The elution resulted in activity of single peak.

FIG. 1 shows the result thus achieved by reverse-phase high performance chromatography. In the diagram, the fraction No. is plotted as abscissa vs. the absorbance at 280 nm and the acetonitrile concentration (%) as ordinate. The active fraction is represented by "H".

The above purification steps are summarized in Table 1 below.

TABLE 1

| Purification step | Total protein amount (mg) | Specific activity (U/μg) | Total activity (U) | Yield (%) |
| --- | --- | --- | --- | --- |
| CCF | 293.60 | 0.5 | 146800 | 100.0 |
| SP-TOYOPEARL | 14.00 | 33.3 | 466667 | 317.9 |
| HA-1000 | 3.63 | 100 | 363000 | 247.3 |
| Protein $C_4$ | 1.98 | 100 | 198000 | 134.9 |

One unit of activity U listed is a minimum activity required for inhibiting the horny membrane formation within 48 hours after the diluted sample was added to 0.3 ml of HCM containing $5 \times 10^5$ epidermal cells, with inhibition of morphological differentiation also achieved.

(4) SDS-PAGE electrophoresis

Sodium dodecylsulfate (SDS)-polyacrylamide gel electrophoresis (PAGE) was conducted according to a modification of the method of Laemmli (Laemmli, U.K., Nature, 227, 680 (1970)).

Concentration of polyacrylamide was 3% for stacking gel, and 10% for separation gel. Coomassie Brilliant Blue (CBB) was used for staining.

The pooled active fractions (CIF of the invention) resulting from the final purification step described above were subjected to SDS-PAGE, which revealed that the CIF was electrophoresed between carbonic anhydrase (molecular weight 31k) and soybean trypsin inhibitor (molecular weight 21.5k) serving as molecular weight markers. This indicated that the CIF is about 24000 daltons in molecular weight.

When repeatedly subjected to SDS-PAGE in the presence or absence of β-mercaptoethanol as a reducing gent, the CIF was stained with CBB as a single band and the electrophoretic profile was not affected by 2-mercaptoethanol. Consequently, the CIF was identified as a single protein having no subunit structure.

(5) Homogeneity of CIF

A 6-μg portion of the sample finally obtained by the foregoing purification step (3), (iii) was applied to a Protein $C_4$ column equilibrated with 0.05% TFA solution containing 10% acetonitrile, followed by linear gradient elution with up to 60% acetonitrile. The resulting eluate exhibited CIF activity of single peak.

Figure 2:
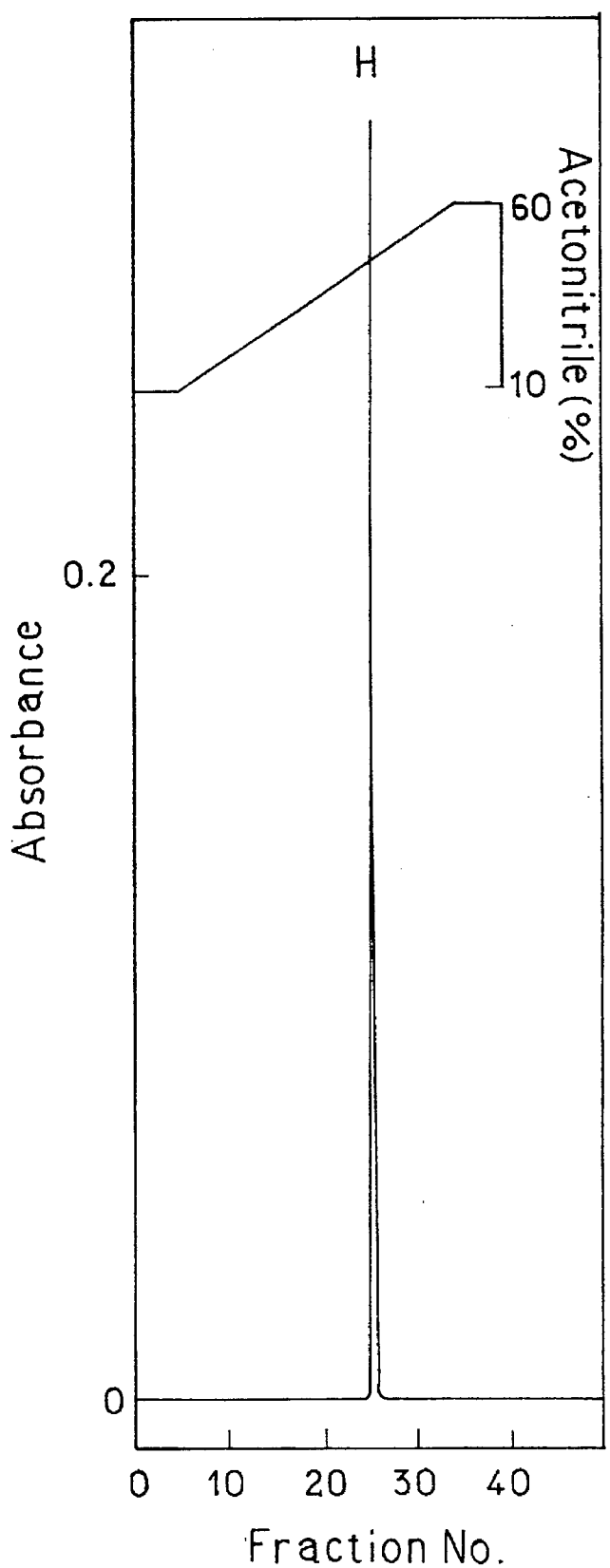
FIG. 2 shows the result of reverse-phase high performance liquid chromatography of the final purified sample of CIF according to Example 1, (5)

FIG. 2, represented similarly to FIG. 1, shows the result of the above reverse-phase high performance liquid chromatography.

(6) Chromatofocusing

A portion of the partially purified sample obtained by the purification step (3), (i) was applied to a PBE94 column (product of Pharmacia LKB Biotechnology AB) equilibrated with 25 mM ethanolamine-acetic acid (pH 9.5), followed by elution with polybuffer 96-acetic acid (pH 6.0) for chromatofocusing in the range of pH 9.0–6.0. The activity was eluted at about pH 8.2.

(7) Activity of CIF to inhibit cornification of epidermal cells

Using the CIF obtained from the final purification step (3), (iii), the minimum quantity required for inhibiting the morphological differentiation of epidermal cells and the cornification thereof was determined by the foregoing method for determination of activity.

Consequently, the minimum quantity was found to be about 0.018 μg protein/ml.

The activity of CIF was found to be reversible as the crude sample mentioned above.

(8) pH stability

Another portion of the partially purified sample obtained from the purification step (3), (i) was dialyzed at 4° C. for 24 hours using 50 mM buffers of pH 2.0 to 11.0 (citrate phosphate buffer: pH 2–6, phosphate buffer: pH 7.0, glycine-NaOH buffer: pH 8–11), followed by dialysis with PBS at 4° C. for 2 hours. The resulting dialyzate was checked for residual activity.

Consequently, the CIF activity was found stable to be in the range of pH 2–10.

(9) Thermal stability

Another portion of the finally purified sample was heat-treated (40°–100° C., 30 min) using DRY THERMOUNIT TAH-1) (Taitec Corporation), then rapidly cooled in an ice bath and thereafter checked for activity.

As a result, the sample was completely inactivated when heat-treated at 60° C. for 30 minutes.

(10) amino acid composition of CIF

A solution containing about 20 μg of purified CIF was placed into a hard glass sample tube (6×40 mm, product of Nippon Electric Glass Co., Ltd.), which was then placed into a hydrolysis reaction vial (product of Pierce Chemical Co.). After drying up the solution in a vacuum, 200 μl of 6N hyrochloric acid (containing 1% of phenol) was placed into the reaction vial, which was evacuated and sealed off, followed by hydrolysis at 130° C. for 4 hours.

After the reaction, 200 μl of Na-S$^{TM}$ solution (product of Beckman instruments Inc.) was placed into the sample tube, the mixture was transferred to an amino acid analysis sample tube, and a 50-μl portion thereof was automatically injected into an amino acid analyzer, Model 6300E (product of Beckman Instruments Inc.) to analyze the amino acid composition. The ninhydrin method was used for detection. No tryptophan is detected by this method.

The amino acids separated and identified were quantitatively determined with reference to calibration curves prepared with use of standard amino acids (1 nanomole), and the amino acid ratio was calculated so that the CIF would be about 24000 in molecular weight and contain 3 phenylalanine residues.

The result obtained is given in Table 2 below.

TABLE 2

| Component amino acids | Amino acid ratio | |
|---|---|---|
|  | Found | Estimated |
| Aspartic acid | 29.9 | 30 |
| Threonine | 14.8 | 15 |
| Serine | 15.1 | 18 |
| Glutamic acid | 19.3 | 19 |
| Proline | 4.9 | 5 |
| Glycine | 13.7 | 14 |
| Alanine | 11.9 | 12 |
| Cystine | 0 | 0 |
| Valine | 11.6 | 13 |
| Methionine | 0.9 | 1 |
| Isoleucine | 9.4 | 12 |
| Leucine | 24.0 | 24 |
| Tyrosine | 13.6 | 14 |
| Phenylalanine | 3.0 | 3 |
| Lysine | 20.9 | 21 |
| Histidine | 0 | 0 |
| Tryptophan | N.D. | 1 |
| Arginine | 9.7 | 10 |

N.D. stands for "not detected."

(11) Amino acid sequence in N-terminal region of CIF

Using a solution containing about 500 picomoles of the purified CIF, the amino acid sequence of CIF was determined up to 45 residues from the N-terminus by a gas-phase protein sequencer (Model 470A, product of Applied Biosystems). The PTH-amino acid solution resulting from each reaction cycle was dried up in a spin-vac evaporater, the solid was dissolved in 33% aqueous solution of acetonitrile, and the amino acids were separated and identified by reverse-phase high performance liquid chromatography for PTH-amino acid analysis (product of Beckman Instruments Inc.).

EXAMPLE 2

(1) Preparation of chromosomal DNA from *Staphylococcus aureus*

A 20-ml quantity of TY medium (1% yeast extract, 1.7% Trypticase, 0.5% NaCl$_1$, 0.25% K$_2$HPO$_4$) was inoculated with a loopful of *Staphylococcus aureus* E-1 subcultured on a slant of Trypticase-soy Broth medium (product of Becton Dickinson and Co., MD, U.S.A.), followed by culture at 37° C. overnight with shaking. The whole amount of the culture solution was inoculated into 500 ml of TY medium and further cultured overnight at 37° C. with shaking.

The resulting culture solution was centrifuged at 4° C. at 5000×g for 10 minutes to collect the cells as a pellet. The cells were then washed with a solution comprising 0.1M Tris-HCl (pH 7.5), 0.1M EDTA and 0.15M NaCl, centrifuged at 4° C. at 2500×g for 10 minutes and collected.

Chromosomal DNA was prepared from the cells thus obtained according to the method-of Marmur (J. Marmur, J. Mol. Biol., 3, 208 (1961)) as described below. The cells were suspended in 40 ml of lysis buffer (0.01M Tris-HCl (pH 7.0), 0.01M MgCl$_2$, 2.5M NaCl), to which 1.7 mg of Lysostaphin (product of Sigma Chemical Company) was added, followed by incubation at 37° C. for 60 minutes. The resulting cell lysate was added 5.32 ml of 25%, SDS and then incubated at 37° C. for 15 minutes. DNA was collected from the resulting solution by extraction with phenol-chloroform and precipitation from ethanol.

The DNA obtained was dissolved in 10 ml of 0.1×SSC (15 mM NaCl, 1.5 mM sodium citrate, pH 7.0), 0.2 ml of 2 mg/ml RNaseA (product of Sigma Chemical Company) was then added to the solution, and the mixture was incubated at 37° C. for 30 minutes. The DNA was collected from the solution by treatment with chloroform isoamyl alcohol and precipitation from ethanol, and subsequently dissolved in 18 ml of 0.1×SSC. Added to the solution were 2 ml of a solution composed of 3M sodium acetate buffer (pH 5.0) and 50 mM of MgCl$_2$ first and then 20 ml of cold isopropanol to precipitate the DNA. The precipitate was collected by winding on a glass rod and then allowed to stand at 4° C. overnight in 70% ethanol. The DNA was dried and then dissolved in 500 μl of TE (10 mM Tris-HCl (pH 8.0), 1 mM EDTA) for use as the chromosomal DNA of *Staphylococcus aureus*.

(2) Screening of CIF gene by Southern blotting

According to the method of Southern (Southern, E., Methods Enzymol., 69, 152 (1980)), the presence of CIF gene in the above solution of chromosomal DNA of *Staphylococcus aureus* was screened.

First, 10 μg of the chromosomal DNA of *Staphylococcus aureus* was incubated with 5 units of restriction endonuclease EcoRI (product of Takara Shuzo Co., Ltd.) at 37° C. for 60 minutes and then the mixture was subjected to agarose gel electrophoresis.

After the electrophoresis, the agarose gel was immersed in a denaturing solution (0.5M NaOH, 1.5M NaCl) for 30 minutes with shaking, and then shaken for 15 minutes twice in a neutralizing solution (0.5M Tris-HCl (pH 7.2), 1.5M NaCl, 1 mM EDTA). The DNA fragments on the gel were then transferred overnight onto a nitrocellulose membrane filter (product of Advantec Toyo Kaisha Ltd.) which had been immersed in 20×SSC (3M NaCl, 0.3M sodium citrate, pH 7.0) solution. The filter was thereafter baked at 80° C. for 2 hours to fix the DNA fragments to the filter.

In corresponding relation to $^{10}$Asp–$^{16}$Gly in the N-terminal amino acid sequence, determined for the CIF isolated and purified from *Staphylococcus aureus* in Example 1, DNAs of 20 bases, i.e., 128 different DNA mixtures represented by the formula below, were synthesized using a DNA synthesizer Model 381A (product of Applied Biosystems), and the 5' end was labeled with $^{32}$P to provide a mixed probe.

Next, the nitrocellulose membrane filter previously obtained was immersed in a prehybridization solution (9 ml of distilled water, 6 ml of 20×SSC, 1 ml of 10% NP-40, 2 ml of 50×Denhardt's, 2 ml of 1 nmg/ml calf thymus DNA and 0.2 ml of 5% sodium pyrophosphate) and preincubated at 65° C. for 3 hours. The mixed probe (1×10$^6$ cpm) labeled at the 5' end and 200 µl of 0.2M EDTA (pH 8.0) were then added to the solution to effect hybridization at 55° C. overnight. After the hybridization, the filter was washed with 6×SSC (0.9M NaCl, 90 nM sodium citrate, pH 7.0) containing 0.05% sodium pyrophosphate and subjected to autoradiography at −80° C. overnight. Consequently, a fragment with which the $^{32}$P-labeled probe had hybridized appeared at the portion of 3.5 kb. This indicated that the fragment contained the CIF gene.

(3) Cloning of CIF gene

Next, the 3.5-kb fragment containing the CIF gene was cloned into EcoRI site of pBR328 (X. Soberon, L. Covarrubias and F. Bolivar, Gene, 9, 287 (1980)) as will be described below.

Ten units of restriction endonuclease EcoRI (product of Takara Shuzo Co., Ltd.) was added to 20 µg of the chromosomal DNA of *Staphylococcus aureus* obtained as already described, and reacted therewith at 37° C. for 1 hour, followed by agarose gel electrophoresis, to obtain 3.5-kb EcoRi fragments containing the CIF gene. Separately, 15 units of restriction endonuclease EcoRI was added to 5 µg of plasmid pBR328 and reacted therewith at 37° C. for 3 hours. One unit of alkaline phosphatase (CIP, product of Boehringer Mannheim GmbH) was added to 5 µg of ECORI fragments of pBR328 obtained and reacted therewith at 37° C. for 30 minutes according to the method of Maniatis et al. (T. Maniatis et al., Molecular Cloning, p. 133, Cold Spring Harbor Laboratory (1982)). One unit of alkali phosphatase was added to the reaction mixture again and reacted therewith at 37° C. for 15 minutes.

A 10-µl quantity of 10×ligase buffer (660 mM Tris-HCl (pH 7.6), 66 mM MgCl$_2$, 100 mM dithiothreitol, 10 mM ATP), 25 µl of 40% polyethylene glycol 6000, and 300 units of T4 DNA ligase (product of Takara Shuzo Co., Ltd.) were added to an aqueous solution which contained 5 µg of EcoRI fragments containing 3.5 kb CIF gene fragment and 5 µg of EcoRI fragments of pBR328 prepared above. The mixture, which was in an amount of 100 µl, was reacted overnight at 16° C.

*E. coli*, WA802 strain (W. B. Wood, J. Mol. Biol., 16, 118 (1966)) was transformed using the resulting reaction mixture. The ligase reaction mixture (100 µl) and 100 µl of a transformation buffer (8% polyethylene glycol 1000, 1 mM EDTA, 0.2M NaCl, 10 mM MOPS) were admixed with 200 µl of a suspension of competent cells of WA802 strain prepared according to the method of Lederberg and Cohen (J. Bacteriol., 119, 1072 (1974)). The mixture was cooled on ice for 60 minutes and then heated in a water bath at 37° C. for 5 minutes. To the mixture was added 0.5 ml of L-broth (1% bactotrypton, 0.5% yeast extract, 0.5% NaCl), and the resulting mixture was incubated at 37° C. for 60 minutes. The suspension (0.9 ml) obtained was then applied to five selection plates, in an amount of 180 µl on each plate, and cultured overnight at 37° C. Each plate was a flat plate medium (25 ml) prepared from L-broth containing 100 µg/ml of ampicillin and 1.5% agar.

The colonies on each of the ampicillin-containing L-broth plates were replicated onto another ampicillin-containing L-broth plates and a L-broth plates containing 100 µg/ml of chloramphenicol and cultured overnight at 37° C. Selected from among the resulting colonies were 3200 ampicillin-resistant chloramphenicol-sensitive colonies growing on the L-broth plate containing ampicillin but not growing on the L-broth plate containing chloramphenicol. The aforementioned $^{32}$P-labeled probe was then hybridized with the selected colonies according to the method of Maniatis et al. (T. Maniatis et al., Molecular Cloning, p.312, Cold Spring Harbor Laboratory (1982)). This procedure afforded 35 positive clones reactive with the probe.

Plasmid DNAs were isolated from the 35 colonies thus obtained, cleaved with restriction endonuclease EcoRI (product of Takara Shuzo Co., Ltd.), and analyzed by Southern blotting. The result indicated that 18 colonies out of 35 colonies had 3.5-kb EcoRI fragments hybridizable to the $^{32}$P-labeled probe. One of these plasmids was named pEDN18.

(4) Determination of DNA sequence of CIF gene

Next, the entire nucleotide sequence corresponding to the CIF coding region of pEDN18 obtained above was determined according to the method of Sanger (Yanish-Perron et al., Gene 33, 103 (1985)) using M13 phage. The result is represented by the formula (2). The formula (2) includes an open reading frame coding for 247 amino acid residue. In this sequence, the sequence-of 35 amino acids from −35 (Met) to −1 (Ala) was found to be a signal sequence for secretory protein by the method of Von Heijne (Nucl. Acids Res., 14, 4683 (1986)).

Further the above amino acid sequence from which the sequence of the signal sequence is removed, i.e., the sequence of 212 amino acid residues (CIF amino acid sequence), is the sequence represented by the formula (1). The N-terminal amino acid sequence of this sequence completely agreed with the N-terminal amino acid sequence of the natural CIF determined in Example 1. Thus, it was proved that the nucleotide sequence of the formula (2) codes for the CIF.

EXAMPLE 3

(1) Synthesis and cloning of α-amylase promoter sequence

For producing recombinant CIF, a DNA fragment represented by the formula (3) below containing the promoter of α-amylase gene (Stephens et al., J. Bacteriol., 158, 369 (1984)) of *Bacillus licheniformis* was chemically synthesized.

More specifically, six kinds of DNA fragments EN-5, EN-6, EN-7, EN-8, EN-9 and EN-10 were synthesized using a DNA synthesizer, Model 381A (product of Applied Biosystems). Subsequently, EN-6, EN-7, EN-9 and EN-10 which were phosphorylated at the 5' end with T4 polynucleotide kinase (product of Takara Shuzo Co., Ltd.), and EN-5 and EN-8 which were not phosphorylated were mixed together, each in an amount of 1 µg, and ligated with T4 DNA ligase to prepare a DNA fragment, having about 112 bp, of promoter of the α-amylase gene represented by the formula (3).

On the other hand, a 5-µg quantity of plasmid pKKO1 (deposited in Fermentation Research Institute, Agency of Industrial Science and Technology with deposition number FERM BP-901) was cleaved with restriction endonuclease EcoRI to prepare a DNA fragment of about 5.75 kb.

The α-amylase gene promoter DNA fragment of about 112 bp and the DNA fragment of about 5.75 kb prepared above were ligated with T4 DNA ligase. The reaction mixture was used to transform *E. coli* HB101 strain (H. W. Boyer, D. Roulland-Dussoix, J. Mol. Biol., 41, 459 (1969)) by the method of Lederberg and Cohen. The resulting suspension containing the transformant was plated onto a flat plate medium (25 ml/plate) prepared from L-broth (10 g/liter of bactotrypton, 5 g/liter of bactoyeast extract, 0.5 g/liter NaCl) containing 100 µg/ml of ampicillin by solidifying the broth with 1.5% agar added thereto, followed by culture overnight at 37° C.

From the plate medium was selected one strain of ampicillin-resistant transformant, from which a plasmid DNA was isolated which was designated pHM04.

Figure 3:
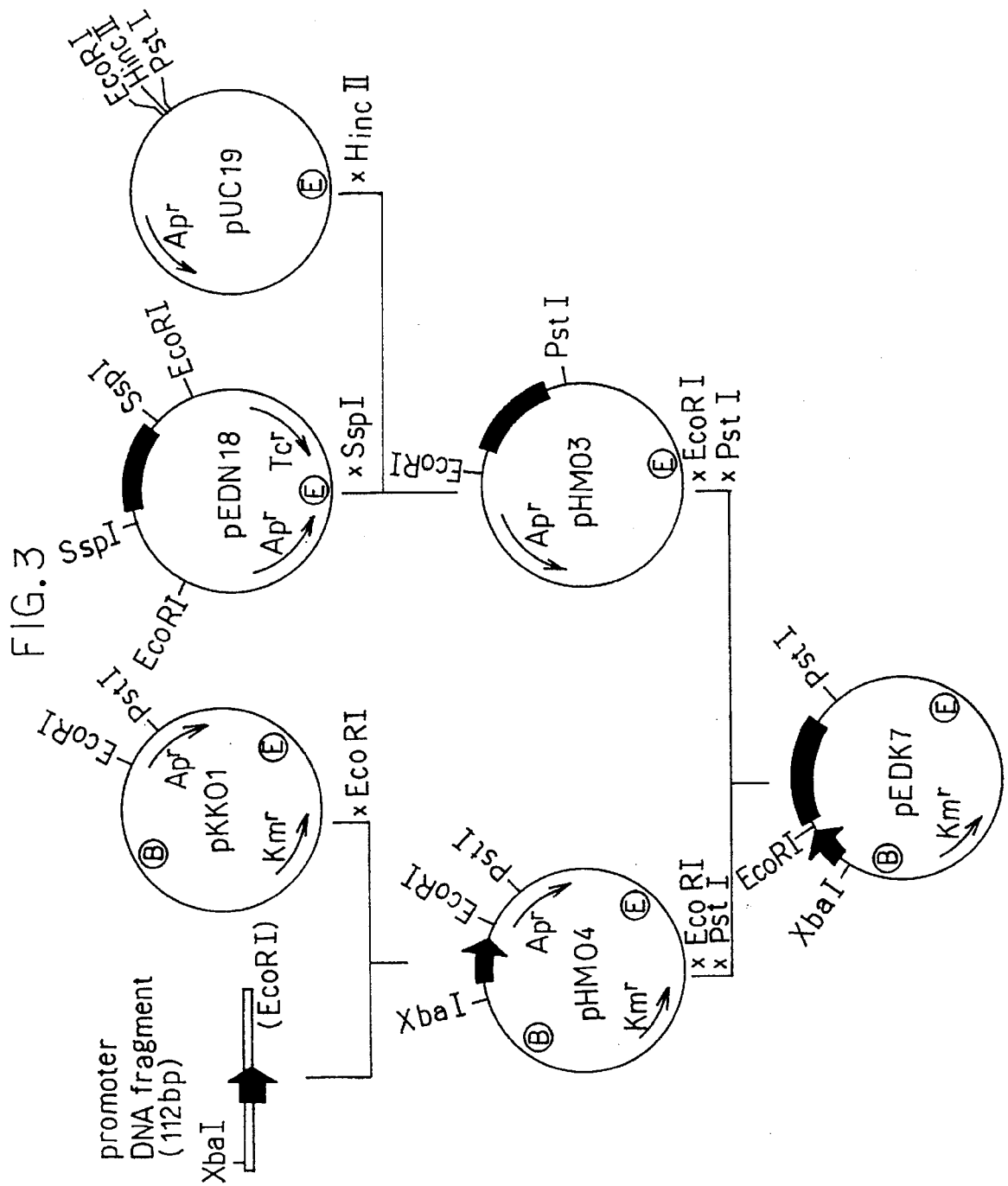
FIG. 3 schematically shows construction of plasmid pHMO4 containing α-amylase promoter according to Example 3, (1), and the construction of CIF expression vector pEDK7 according to Example 3, (2). In the drawing, the gene of a CIF precursor is represented by ■, α-anylase promoter by ➡, an ampicillin-resistant gene (Ap$^r$) or kanamycin-resistant gene (Km$^r$) by →, and the replication origin regions of *E. coli* and *Bacillus subtilis* by E and B, respectively.

Agarose gel electrophoresis revealed that the plasmid pEM04 had a size of about 5.76 kb. With reference to FIG. 3, it was also found that the plasmid had an α-amylase promoter upstream of an ampicillin-resistant gene, and further had both replication origin regions for *E. coli* and *Bacillus subtillis*.

(2) Preparation of CIF expression vector

As will be apparent from the formula (2), the gene of the CIF precursor can be cut out from the plasmid pEDN18 having the CIF precursor gene using restriction endonuclease SspI.

First, 6 units of restriction endonuclease SspI (product of Takara Shuzo Co., Ltd.) was added to 10 µg of pEDN18 and reacted therewith at 37° C. for 3 hours to prepare a DNA fragment having about 865 bp and containing the CIF precursor gene.

Separately, 10 units of restriction endonuclease HinCII (product of Takara Shuzo Co., Ltd.) was added to plasmid pUC19 (product of Takara Shuzo Co., Ltd.) and reacted therewith at 37° C. for 3 hours to prepare a vector DNA fragment of about 2.7 kb.

The DNA fragment of about 865 bp containing the CIF precursor gene and the vector DNA fragment of about 2.7 kb thus obtained were ligated with T4 DNA ligase. *E. coli* JM109 strain (product of Takara Shuzo Co., Ltd.) was transformed with the reaction mixture by the method of Lederberg and Cohen. In the same manner as above, one strain of ampicillin-resistant transformant was selected from among those cultured on a plate medium containing ampicillin (100 µg/ml). A plasmid DNA was isolated from the transformant and designated pHM03.

Agarose gel electrophoresis revealed that the plasmid pHM03 was about 3.55 kb in size. With reference to FIG. 3, it was found that the plasmid had a structure wherein the CIF precursor gene was inserted in the vector pUC19, and that the CIF precursor gene can be cut out again by cleaving the plasmid with two kinds of restriction endonucleases EcoRI and PstI.

pMH03 (10 αg) thus obtained was reacted with restriction endonucleases EcoRI and PstI (products of Takara Shuzo Co., Ltd.) at 37° C. for 3 hours in a high salt concentration buffer (50 mM tris-HCl (pH 7.5), 100 mM NaCl, 10 mM MgCl$_2$, 1 mM dithiothreitol) to prepare a DNA fragment of about 0.9 kb containing the CIF precursor gene. Further similarly, 5 µg of pHM04 was cleaved with EcoRI and PstI to prepare a vector DNA fragment of about 5.01 kb. T4 DNA ligase (350 units) was added to an aqueous solution of mixture of these two DNA fragments obtained to ligate the DNA fragments. *E. coli* HB101 strain was transformed with the resulting reaction mixture by the method of Lederberg and Cohen. One strain of kanamycin-resistant transformant was selected from among those cultured on a plate-medium having kanamycin (5 µg/ml) added thereto. A plasmid DNA was isolated from the transformant and designated pEDK7.

Agarose gel electrophoresis revealed that the plasmid pEDK7 was about 5.91 kb in size. With reference to FIG. 3, it was found that the plasmid had a structure wherein the CIF precursor gene was positioned downstream of the α-amylase promoter and which further had both replication origin regions for *E. coli* and *Bacillus subtilis* and a kanamycin-resistant gene.

*Bacillus subtilis* IA182 strain was transformed with the plasmid pEDK7 thus obtained. The *Bacillus subtilis* IA182 strain (Yoneda, Y. et al., Biochem. Biophys. Res. Commun., 50, 765 (1973)) was provided by Ohio State University, Bacillus Genetic Stock Center, a public strain preserving organization.

For transformation, *Bacillus subtilis* was converted to protoplasts by treatment with lysozyme. More specifically, *Bacillus subtilis* IA182 strain was precultured in L broth overnight at 30° C. A 50-ml quantity of L broth was inoculated with 1 ml of the precultured solution, which was then cultured at 30° C. for 3 hours with shaking. The culture solution was centrifuged (7000 r.p.m.) for 5 minutes. The cells collected were suspended in 5 ml of SMMP solution (0.5M sucrose, 20 mM sodium maleate (pH 6.5), 20 mM MgI$_2$, 0.35% Penassay broth (product of Difco Laboratories). With addition of 10 mg of lysozyme (product of Sigma Chemical Company), the suspension was maintained at 37° C. for 1 hour. A microscopic observation revealed that at least 90% of the cells were converted to protoplasts, whereon the cells were collected by centrifugation 3000 r.p.m., 5 min), washed with 5 ml of SMMP solution once and then suspended in 5 ml of SMMP solution. A 0.5-ml portion of the suspension and 0.1 ml of an aqueous solution containing 10 µg of plasmid pEDK7 were mixed together. To the mixture was added 1.4 ml of a polyethylene glycol solution (40% polyethylene glycol 6000 (product of Wako Pure Chemical Industries Inc.), 0.5M sucrose, 20 mM sodium maleate (pH 6.5), 20 mM MgCl$_2$), and the resulting mixture was agitated up and down for 2 minutes. With addition of 5 ml of SMMP solution, the mixture was centrifuged (3000 r.p.m., 15 minutes) to obtain protoplasts, which were suspended in 1 ml of SMMP solution. The suspension was allowed to stand at 30° C. for 90 minutes and then diluted with SMMP solution 10- to 1000-fold. A 0.2 ml portion of the dilution was thereafter applied to DM3 medium having the following composition and cultured at 30° C. for 24 hours. The grown *Bacillus subtilis* was isolated as a transformant.

| <Composition of DM3 medium> | |
| --- | --- |
| Sodium succinate | 135.1 g/liter |
| Casamino acid | 5.0 |
| Bacto yeastextract | 5.0 |
| Glucose | 5.0 |
| Potassium dihydrogen phosphate | 1.5 |
| Potassium hydrogen phosphate | 3.5 |
| Magnesium chloride | 4.1 |
| Bovine serum albumin | 0.1 |
| Agar | 8.0 |
| Kanamycin sulfate | 0.3 |

*Bacillus subtilis* IA182 harboring the plasmid pEDK7 and thus obtained is deposited with the designation "IA182

(pEDK7)" in Fermentation Research Institute, Agency of Industrial Science and Technology, MITI. The deposition number is FERM BP-3025.

The strain IA182 of *Bacillus subtilis* harboring the plasmid pEDK7 was cultured at 30° C. in 3 liters of Soytone phosphate medium (20 g/liter of Bacto soytone, g/liter of glucose, 5 g/liter of NaCl, 2.5 g/liter of $Na_2HPO_3$, pH 7.3) in a 5-liter jar fermenter (Model MD300-5L, product of B. E. Marubishi Co, Ltd.). Approximately 10-ml portions of the culture solution were collected 10, 11.5 and 13 hours later and centrifuged to prepare supernatants.

(3) Quantitative determination of CIF by ELISA

The culture supernatants obtained by the procedure (2) were ascertained the presence of the CIF therein by ELISA.

a) Preparation of anti-CIF serum

A rabbit was immunized with purified CIF (hereinafter referred to as "standard CIF") as an antigen to prepare anti-serum EDN-001 containing CIF antibodies. More specifically, 0.4 ml of complete Freund's adjuvant (product of Difco Laboratory) was added to 0.4 ml of 50 mM phosphate buffer (pH 6.9) containing 80 µg of standard CIF to prepare an emulsion; which was subcutaneously injected into the chest of the rabbit. This procedure was repeated every two weeks four times, 80 µg of standard CIF was thereafter given intravenously, the whole blood was collected 3 days later, and the serum was separated off.

b) Preparation of anti-CIF-IgG and enzyme-labeled antibody

Using MAPSII Kit (product of Bio-Rad Laboratories), 91.2 mg of purified IgG was prepared from 10 ml of the anti-serum EDN-001 obtained by the step a). Half of the purified IgG was dialyzed against 100 mM phosphate buffer (pH 7.0), and the dialyzate was dividedly preserved as IgG for coating use. Subsequently, 1.5 mg of pepsin was added to 100 mM of sodium acetate buffer (pH 4.5) containing 37.5 mg of IgG and reacted therewith at 37° C. for 48 hours. The reaction mixture was adjusted to pH 7.0 with 0.1N sodium hydroxide and applied to AcA44 column (1.5×45 cm, product of IBF Biotechniques), followed by elution with 100 mM phosphate buffer (pH 7.0). To 6 ml of 100 mM phosphate buffer (pH 6.0) containing 18.5 mg of the obtained F(ab')2 was added 666 µl of 100 mM phosphate buffer containing 100 mM 2-mercaptoethanol and 1 mM EDTA, and the mixture was reacted at 37° C. for 90 minutes. The reaction mixture was then purified by Sephadex G-75 column.(1.5× 45 cm) to obtain 17 mg of Fab'.

Separately, 0.2 ml of dimethylformamide containing 80 mM N-(ε-maleimidocaproyloxy-succinimide was added to 1.9 ml of 100 mM phosphate buffer (pH 7.0) containing 27.5 mg of horse-radish peroxidase (hereinafter referred to as "POD", product of Toyobo Co., Ltd.) and reacted therewith at 37° C. for 30 minutes. The reaction mixture was then purified by Sephadex G-75 column (1.5×45 cm), giving 19 mg of POD having maleimido group introduced therein (hereinafter referred to as "POD-mal").

A 3-mg quantity of Fab' and a 5.4-mg portion of POD-mal obtained were mixed together and reacted at 4° C. for 23 hours. With addition of 12 µl of 50 mM N-ethylmaleimide, the reaction mixture was purified by AcA44 column (1.5×45 cm) to obtain 1.2 mg of an enzyme labeled antibody (hereinafter referred to as "Fab'-POD"). To Fab'-POD prepared were added70.5% bovine serum albumin (BSA, product of Sigma Chemical Company), 0.05% thimerosal and 10% normal rabbit serum, and the mixture was dividedly frozen for preservation.

c) Quantitative determination of CIF

The igG obtained by the above step for coating use was diluted with phosphate-buffered saline (PBS) to a concentration of 20 µg/ml, and the dilution was placed onto a 96-well microplate (product of Nunc Inc.), in an amount of 100 µl in each well, and allowed to stand overnight at 4° C. The plate was then washed with running water, and 300 µl of PBS containing 1% BSA was placed into each well and allowed to stand at 4° C. overnight. Subsequently, the wells were washed with PBS containing 0.05% polyoxyethylene (20) sorbitan monolaurate (product of Wako Pure Chemical Industries, Ltd.), and standard CIF or a test sample diluted with PBS containing 0.1% BSA was thereafter added to the wells, in an amount of 100 µl in each well, and allowed to stand at 4° C. overnight. The solution was then removed from the wells, which were thereafter washed with PBS containing 0.05% Tween 20. Next, 100 µl of Fab'-POD diluted 100-fold with PBS containing 0.1% BSA was placed into each well and allowed to stand at room temperature for 4 hours. The solution was removed from the well again, and the well was washed with PBS containing 0.05% Tween 20 and further with PBS. Thereafter, 100 µl of 100 mM citrate-phosphate buffer (pH 5.0) containing 0.25% o-phenylenediamine and 0.15% hydrogen peroxide was placed into the well, followed by reaction at room temperature for 15 minutes. Finally, 100 µl of 1N sulfuric acid was added to each well.

The CIF content of the sample was determined from a dilution curve of standard CIF obtained by measuring the absorbance at 492 nm. The result is given below.

| Culturing time (hours) | 10 | 11.5 | 13 |
|---|---|---|---|
| CIF content (mg/liter) | 8.7 | 11.1 | 21.3 |

The above result indicates that the culture supernatant of *Bacillus subtilis*, IA183 strain harboring the plasmid pEDK7 contained a considerable amount of CIF produced. The CIF isolated from the supernatant and purified was identical with the CIF (natural type) produced by *Staphylococcus aureus* E-1 physicochemically and immunochemically.

---

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 212 amino acids
        ( B ) TYPE: amino acid (C) STRANDEDNESS: single
(D) TOPOLOGY: unknown (ii) MOLECULE TYPE: peptide (iii) HYPOTHETICAL: YES (xi) SEQUENCE DESCRIPTION: SEQ ID NO:1:

| Ala | Asp | Val | Lys | Asn | Phe | Thr | Asp | Leu | Asp | Glu | Ala | Thr | Lys | Trp | Gly |
|---|---|---|---|---|---|---|---|---|---|---|---|---|---|---|---|
| 1 | | | | 5 | | | | | 10 | | | | | 15 | |

| Asn | Lys | Leu | Ile | Lys | Gln | Ala | Lys | Tyr | Ser | Ser | Asp | Asp | Lys | Ile | Ala |
|---|---|---|---|---|---|---|---|---|---|---|---|---|---|---|---|
| | | | 20 | | | | | 25 | | | | | 30 | | |

| Leu | Tyr | Glu | Tyr | Thr | Lys | Asp | Ser | Ser | Lys | Ile | Asn | Gly | Pro | Leu | Arg |
|---|---|---|---|---|---|---|---|---|---|---|---|---|---|---|---|
| | | 35 | | | | | 40 | | | | | 45 | | | |

| Leu | Ala | Gly | Gly | Asp | Ile | Asn | Lys | Leu | Asp | Ser | Thr | Thr | Gln | Asp | Lys |
|---|---|---|---|---|---|---|---|---|---|---|---|---|---|---|---|
| | 50 | | | | | 55 | | | | | 60 | | | | |

| Val | Arg | Arg | Leu | Asp | Ser | Ser | Ile | Ser | Lys | Ser | Thr | Thr | Pro | Glu | Ser |
|---|---|---|---|---|---|---|---|---|---|---|---|---|---|---|---|
| 65 | | | | | 70 | | | | | 75 | | | | | 80 |

| Val | Tyr | Val | Tyr | Arg | Leu | Leu | Asn | Leu | Asp | Tyr | Leu | Thr | Ser | Ile | Val |
|---|---|---|---|---|---|---|---|---|---|---|---|---|---|---|---|
| | | | | 85 | | | | | 90 | | | | | 95 | |

| Gly | Phe | Thr | Asn | Glu | Asp | Leu | Tyr | Lys | Leu | Gln | Gln | Thr | Asn | Asn | Gly |
|---|---|---|---|---|---|---|---|---|---|---|---|---|---|---|---|
| | | | 100 | | | | | 105 | | | | | 110 | | |

| Gln | Tyr | Asp | Glu | Asn | Leu | Val | Arg | Lys | Leu | Asn | Asn | Val | Met | Asn | Ser |
|---|---|---|---|---|---|---|---|---|---|---|---|---|---|---|---|
| | | | 115 | | | | | 120 | | | | | 125 | | |

| Arg | Ile | Tyr | Arg | Glu | Asp | Gly | Tyr | Ser | Ser | Thr | Gln | Leu | Val | Ser | Gly |
|---|---|---|---|---|---|---|---|---|---|---|---|---|---|---|---|
| | | | 130 | | | | | 135 | | | | | 140 | | |

| Ala | Ala | Val | Gly | Gly | Arg | Pro | Ile | Glu | Leu | Arg | Leu | Glu | Leu | Pro | Lys |
|---|---|---|---|---|---|---|---|---|---|---|---|---|---|---|---|
| 145 | | | | | 150 | | | | | 155 | | | | | 160 |

| Gly | Thr | Lys | Ala | Ala | Tyr | Leu | Asn | Ser | Lys | Asp | Leu | Thr | Ala | Tyr | Tyr |
|---|---|---|---|---|---|---|---|---|---|---|---|---|---|---|---|
| | | | | 165 | | | | | 170 | | | | | 175 | |

| Gly | Gln | Gln | Glu | Val | Leu | Leu | Pro | Arg | Gly | Thr | Glu | Tyr | Ala | Val | Gly |
|---|---|---|---|---|---|---|---|---|---|---|---|---|---|---|---|
| | | | | 180 | | | | | 185 | | | | | 190 | |

| Ser | Val | Glu | Leu | Ser | Asn | Asp | Lys | Lys | Lys | Ile | Ile | Ile | Thr | Ala | Ile |
|---|---|---|---|---|---|---|---|---|---|---|---|---|---|---|---|
| | | | 195 | | | | | 200 | | | | | 205 | | |

| Val | Phe | Lys | Lys |
|---|---|---|---|
| | 210 | | |

(2) INFORMATION FOR SEQ ID NO:2:

(i) SEQUENCE CHARACTERISTICS:
(A) LENGTH: 247 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:2:

| Met | Lys | Asn | Lys | Leu | Leu | Phe | Lys | Ile | Phe | Leu | Ser | Leu | Ser | Leu | Ala |
|---|---|---|---|---|---|---|---|---|---|---|---|---|---|---|---|
| 1 | | | | 5 | | | | | 10 | | | | | 15 | |

| Leu | Ser | Val | Tyr | Ser | Ile | Asn | Asp | Lys | Ile | Ile | Glu | Val | Ser | Asn | Thr |
|---|---|---|---|---|---|---|---|---|---|---|---|---|---|---|---|
| | | | | 20 | | | | | 25 | | | | | 30 | |

| Ser | Leu | Ala | Ala | Asp | Val | Lys | Asn | Phe | Thr | Asp | Leu | Asp | Glu | Ala | Thr |
|---|---|---|---|---|---|---|---|---|---|---|---|---|---|---|---|
| | | | 35 | | | | | 40 | | | | | 45 | | |

| Lys | Trp | Gly | Asn | Lys | Leu | Ile | Lys | Gln | Ala | Lys | Tyr | Ser | Ser | Asp | Asp |
|---|---|---|---|---|---|---|---|---|---|---|---|---|---|---|---|
| | 50 | | | | | 55 | | | | | 60 | | | | |

| Lys | Ile | Ala | Leu | Tyr | Glu | Tyr | Thr | Lys | Asp | Ser | Ser | Lys | Ile | Asn | Gly |
|---|---|---|---|---|---|---|---|---|---|---|---|---|---|---|---|
| 65 | | | | | 70 | | | | | 75 | | | | | 80 |

| Pro | Leu | Arg | Leu | Ala | Gly | Gly | Asp | Ile | Asn | Lys | Leu | Asp | Ser | Thr | Thr |

|   |   |   |   |   | 85 |   |   |   |   | 90 |   |   |   |   | 95 |   |   |
|---|---|---|---|---|---|---|---|---|---|---|---|---|---|---|---|---|---|
| Gln | Asp | Lys | Val<br>100 | Arg | Arg | Leu | Asp | Ser<br>105 | Ser | Ile | Ser | Lys | Ser<br>110 | Thr | Thr |
| Pro | Glu | Ser<br>115 | Val | Tyr | Val | Tyr | Arg<br>120 | Leu | Leu | Asn | Leu | Asp<br>125 | Tyr | Leu | Thr |
| Ser | Ile<br>130 | Val | Gly | Phe | Thr | Asn<br>135 | Glu | Asp | Leu | Tyr | Lys<br>140 | Leu | Gln | Gln | Thr |
| Asn<br>145 | Asn | Gly | Gln | Tyr | Asp<br>150 | Glu | Asn | Leu | Val | Arg<br>155 | Lys | Leu | Asn | Asn | Val<br>160 |
| Met | Asn | Ser | Arg | Ile<br>165 | Tyr | Arg | Glu | Asp | Gly<br>170 | Tyr | Ser | Ser | Thr | Gln<br>175 | Leu |
| Val | Ser | Gly | Ala<br>180 | Ala | Val | Gly | Gly | Arg<br>185 | Pro | Ile | Glu | Leu | Arg<br>190 | Leu | Glu |
| Leu | Pro | Lys<br>195 | Gly | Thr | Lys | Ala | Ala<br>200 | Tyr | Leu | Asn | Ser | Lys<br>205 | Asp | Leu | Thr |
| Ala | Tyr<br>210 | Tyr | Gly | Gln | Gln | Glu<br>215 | Val | Leu | Leu | Pro | Arg<br>220 | Gly | Thr | Glu | Tyr |
| Ala<br>225 | Val | Gly | Ser | Val | Glu<br>230 | Leu | Ser | Asn | Asp | Lys<br>235 | Lys | Lys | Ile | Ile | Ile<br>240 |
| Thr | Ala | Ile | Val | Phe<br>245 | Lys | Lys |   |   |   |   |   |   |   |   |   |

( 2 ) INFORMATION FOR SEQ ID NO:3:

( i ) SEQUENCE CHARACTERISTICS:
        ( A ) LENGTH: 636 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:3:

```
GCTGATGTTA AAAATTTCAC TGATTTAGAT GAGGCAACTA AATGGGGGAA TAAACTTATA    60
AAACAAGCTA AGTATAGTTC GGATGATAAA ATAGCTCTAT ACGAATATAC AAAAGATAGT   120
TCTAAGATAA ATGGTCCATT AAGACTCGCA GGTGGAGATA TTAATAAGCT AGATTCAACA   180
ACTCAAGACA AGTAAGAAG  ATTAGATTCA TCTATTTCTA AATCTACTAC TCCTGAATCT   240
GTATACGTTT ATAGACTTTT AAATTTAGAT TATTTGACAA GTATCGTTGG ATTTACAAAT   300
GAAGATTTAT ATAAATTACA ACAGACCAAT AATGGCCAGT ATGATGAAAA TCTAGTTAGA   360
AAGCTTAATA ACGTTATGAA TAGCAGAATA TATAGAGAAG ACGGATACTC TAGTACACAA   420
TTAGTTAGTG GAGCAGCTGT AGGTGGTAGA CCTATTGAAT TAAGGTTAGA ATTACCAAAA   480
GGGACTAAAG CTGCGTATCT TAATTCTAAA GATTTAACTG CTTACTATGG TCAACAAGAA   540
GTTTTATTAC CTAGAGGCAC AGAATACGCT GTTGGAAGTG TAGAATTGTC AAATGATAAA   600
AAGAAAATCA TAATAACAGC TATTGTTTTT AAAAAA                             636
```

( 2 ) INFORMATION FOR SEQ ID NO:4:

( i ) SEQUENCE CHARACTERISTICS:
        ( A ) LENGTH: 899 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:4:

5,654,171

-continued

| AAAAACAGAA | TAAATATTTT | CTTTTAATAA | TAAAATATCA | TATAATGAAA | TTATATATAA | 60 |
| AAAACAATCA | AGAGGAGATT | TTTATGAAAA | ACAAATTACT | TTTTAAAATT | TTTTTGAGTT | 120 |
| TATCTTTAGC | ATTAAGCGTT | TATTCAATTA | ATGATAAAAT | CATAGAAGTA | TCTAATACTT | 180 |
| CTTTAGCAGC | TGATGTTAAA | AATTTCACTG | ATTTAGATGA | GGCAACTAAA | TGGGGGAATA | 240 |
| AACTTATAAA | ACAAGCTAAG | TATAGTTCGG | ATGATAAAAT | AGCTCTATAC | GAATATACAA | 300 |
| AAGATAGTTC | TAAGATAAAT | GGTCCATTAA | GACTCGCAGG | TGGAGATATT | AATAAGCTAG | 360 |
| ATTCAACAAC | TCAAGACAAA | GTAAGAAGAT | TAGATTCATC | TATTTCTAAA | TCTACTACTC | 420 |
| CTGAATCTGT | ATACGTTTAT | AGACTTTTAA | ATTTAGATTA | TTTGACAAGT | ATCGTTGGAT | 480 |
| TTACAAATGA | AGATTTATAT | AAATTACAAC | AGACCAATAA | TGGCCAGTAT | GATGAAAATC | 540 |
| TAGTTAGAAA | GCTTAATAAC | GTTATGAATA | GCAGAATATA | TAGAGAAGAC | GGATACTCTA | 600 |
| GTACACAATT | AGTTAGTGGA | GCAGCTGTAG | GTGGTAGACC | TATTGAATTA | AGGTTAGAAT | 660 |
| TACCAAAAGG | GACTAAAGCT | GCGTATCTTA | ATTCTAAAGA | TTTAACTGCT | TACTATGGTC | 720 |
| AACAAGAAGT | TTTATTACCT | AGAGGCACAG | AATACGCTGT | TGGAAGTGTA | GAATTGTCAA | 780 |
| ATGATAAAAA | GAAAATCATA | ATAACAGCTA | TTGTTTTTAA | AAAATAGAAA | TATAAACAAA | 840 |
| GTAATAACAA | GGATTAATAA | ATTAAAAATT | TTAATTAATA | TTTCTATAA | CTAAAAGAA | 899 |

We claim:

1. An isolated and purified polypeptide comprising a sequence of 212 amino acid residues represented by the following formula (1) and a molecular weight of about 24000 daltons as determined by SDS-PAGE. Formula (1):

```
1                                           10
Ala Asp Val Lys Asn Phe Thr Asp Leu Asp
11                                          20
Glu Ala Thr Lys Trp Gly Asn Lys Leu Ile
21                                          30
Lys Gln Ala Lys Tyr Ser Ser Asp Asp Lys
31                                          40
Ile Ala Leu Tyr Glu Tyr Thr Lys Asp Ser
41                                          50
Ser Lys Ile Asn Gly Pro Leu Arg Leu Ala
51                                          60
Gly Gly Asp Ile Asn Lys Leu Asp Ser Thr
61                                          70
Thr Gln Asp Lys Val Arg Arg Leu Asp Ser
71                                          80
Ser Ile Ser Lys Ser Thr Thr Pro Glu Ser
81                                          90
Val Tyr Val Tyr Arg Leu Leu Asn Leu Asp
91                                          100
Tyr Leu Thr Ser Ile Val Gly Phe Thr Asn
101                                         110
Glu Asp Leu Tyr Lys Leu Gln Gln Thr Asn
111                                         120
Asn Gly Gln Tyr Asp Glu Asn Leu Val Arg
121                                         130
Lys Leu Asn Asn Val Met Asn Ser Arg Ile
131                                         140
Tyr Arg Glu Asp Gly Tyr Ser Ser Thr Gln
141                                         150
Leu Val Ser Gly Ala Ala Val Gly Gly Arg
151                                         160
Pro Ile Glu Leu Arg Leu Glu Leu Pro Lys
161                                         170
Gly Thr Lys Ala Ala Tyr Leu Asn Ser Lys
171                                         180
Asp Leu Thr Ala Tyr Tyr Gly Gln Gln Glu
181                                         190
Val Leu Leu Pro Arg Gly Thr Glu Tyr Ala
191                                         200
Val Gly Ser Val Glu Leu Ser Asn Asp Lys
201                                         210
Lys Lys Ile Ile Ile Thr Ala Ile Val Phe
211 212
Lys Lys
```

2. An isolated and purified DNA sequence coding for the amino acid sequence defined in claim 1.

3. An isolated and purified DNA sequence as defined in claim 2 and represented by the following formula:

```
GCT GAT GTT AAA AAT TTC ACT GAT TTA GAT
GAG GCA ACT AAA TGG GGG AAT AAA CTT ATA
AAA CAA GCT AAG TAT AGT TCG GAT GAT AAA
ATA GCT CTA TAC GAA TAT ACA AAA GAT AGT
TCT AAG ATA AAT GGT CCA TTA AGA CTC GCA
GGT GGA GAT ATT AAT AAG CTA GAT TCA ACA
ACT CAA GAC AAA GTA AGA AGA TTA GAT TCA
TCT ATT TCT AAA TCT ACT ACT CCT GAA TCT
GTA TAC GTT TAT AGA CTT TTA AAT TTA GAT
TAT TTG ACA AGT ATC GTT GGA TTT ACA AAT
GAA GAT TTA TAT AAA TTA CAA CAG ACC AAT
AAT GGC CAG TAT GAT GAA AAT CTA GTT AGA
AAG CTT AAT AAC GTT ATG AAT AGC AGA ATA
TAT AGA GAA GAC GGA TAC TCT AGT ACA CAA
TTA GTT AGT GGA GCA GCT GTA GGT GGT AGA
CCT ATT GAA TTA AGG TTA GAA TTA CCA AAA
GGG ACT AAA GCT GCG TAT CTT AAT TCT AAA
GAT TTA ACT GCT TAC TAT GGT CAA CAA GAA
GTT TTA TTA CCT AGA GGC ACA GAA TAC GCT
GTT GGA AGT GTA GAA TTG TCA AAT GAT AAA
AAG AAA ATC ATA ATA ACA GCT ATT GTT TTT
AAA AAA
```

4. An expression vector having a DNA sequence coding for the amino acid sequence defined in claim 1.

5. A DNA sequence coding for the amino acids of a fusion protein composed of the polypeptide defined in claim 1 and a signal sequence.

6. A DNA sequence defined in claim 5 and represented by the following formula:

```
ATG AAA AAC AAA TTA CTT TTT AAA ATT TTT
Met Lys Asn Lys Leu Leu Phe Lys Ile Phe
-35                                    -26

TTG AGT TTA TCT TTA GCA TTA AGC GTT TAT
Leu Ser Leu Ser Leu Ala Leu Ser Val Tyr
-25                                    -16

TCA ATT AAT GAT AAA ATC ATA GAA GTA TCT
Ser Ile Asn Asp Lys Ile Ile Glu Val Ser
-15                                     -6

AAT ACT TCT TTA GCA GCT GAT GTT AAA AAT
Asn Thr Ser Leu Ala Ala Asp Val Lys Asn
-5              -1   1                  5

TTC ACT GAT TTA GAT GAG GCA ACT AAA TGG
Phe Thr Asp Leu Asp Glu Ala Thr Lys Trp
6                                      15

GGG AAT AAA CTT ATA AAA CAA GCT AAG TAT
Gly Asn Lys Leu Ile Lys Gln Ala Lys Tyr
16                                     25

AGT TCG GAT GAT AAA ATA GCT CTA TAC GAA
Ser Ser Asp Asp Lys Ile Ala Leu Tyr Glu
26                                     35

TAT ACA AAA GAT AGT TCT AAG ATA AAT GGT
Tyr Thr Lys Asp Ser Ser Lys Ile Asn Gly
36                                     45

CCA TTA AGA CTC GCA GGT GGA GAT ATT AAT
Pro Leu Arg Leu Ala Gly Gly Asp Ile Asn
46                                     55

AAG CTA GAT TCA ACA ACT CAA GAC AAA GTA
Lys Leu Asp Ser Thr Thr Gln Asp Lys Val
56                                     65

AGA AGA TTA GAT TCA TCT ATT TCT AAA TCT
Arg Arg Leu Asp Ser Ser Ile Ser Lys Ser
66                                     75

ACT ACT CCT GAA TCT GTA TAC GTT TAT AGA
Thr Thr Pro Glu Ser Val Tyr Val Tyr Arg
76                                     85

CTT TTA AAT TTA GAT TAT TTG ACA AGT ATC
Leu Leu Asn Leu Asp Tyr Leu Thr Ser Ile
86                                     95

GTT GGA TTT ACA AAT GAA GAT TTA TAT AAA
Val Gly Phe Thr Asn Glu Asp Leu Tyr Lys
96                                    105

TTA CAA CAG ACC AAT AAT GGC CAG TAT GAT
Leu Gln Gln Thr Asn Asn Gly Gln Tyr Asp
106                                   115

GAA AAT CTA GTT AGA AAG CTT AAT AAC GTT
Glu Asn Leu Val Arg Lys Leu Asn Asn Val
116                                   125

ATG AAT AGC AGA ATA TAT AGA GAA GAC GGA
Met Asn Ser Arg Ile Tyr Arg Glu Asp Gly
126                                   135

TAC TCT AGT ACA CAA TTA GTT AGT GGA GCA
Tyr Ser Ser Thr Gln Leu Val Ser Gly Ala
136                                   145

GCT GTA GGT GGT AGA CCT ATT GAA TTA AGG
Ala Val Gly Gly Arg Pro Ile Glu Leu Arg
146                                   155

TTA GAA TTA CCA AAA GGG ACT AAA GCT GCG
Leu Glu Leu Pro Lys Gly Thr Lys Ala Ala
156                                   165

TAT CTT AAT TCT AAA GAT TTA ACT GCT TAC
Tyr Leu Asn Ser Lys Asp Leu Thr Ala Tyr
166                                   175

TAT GGT CAA CAA GAA GTT TTA TTA CCT AGA
Tyr Gly Gln Gln Glu Val Leu Leu Pro Arg
176                                   185

GGC ACA GAA TAC GCT GTT GGA AGT GTA GAA
Gly Thr Glu Tyr Ala Val Gly Ser Val Glu
186                                   195

TTG TCA AAT GAT AAA AAG AAA ATC ATA ATA
Leu Ser Asn Asp Lys Lys Lys Ile Ile Ile
196                                   200

ACA GCT ATT GTT TTT AAA AAA TAG.
Thr Ala Ile Val Phe Lys Lys ***
206                           212
```

7. An expression vector having the DNA sequence defined in claim 5.

8. A transformant harboring the expression vector defined in claim 4.

9. A transformant as defined in claim 8 provided by a procaryotic organism as the host.

10. A transformant as defined in claim 8 provided by *E. coli* or *Bacillus subtilis* as the host.

11. A transformant as defined in claim 10 which is a strain deposited in Fermentation Research Institute as No.3025 (FERM BP-3025).

12. A process for preparing the polypeptide as defined in claim 1 characterized by culturing a transformant harboring an expression vector under conditions permitting expression of the desired polypeptide, the expression vector having a DNA sequence coding for the amino acid sequence of the formula (1), and isolating the polypeptide from the resulting culture mixture.

13. A pharmaceutical composition characterized in that the composition comprises the polypeptide defined in claim 1 as an active component.

14. A pharmaceutical composition as defined in claim 13 which is an agent for inhibiting cornification of the skin.

15. A cosmetic comprising the polypeptide defined in claim 1.

16. A method of inhibiting abnormal cornification of the skin by applying thereto an effective amount of the polypeptide defined in claim 1.

* * * * *

UNITED STATES PATENT AND TRADEMARK OFFICE
CERTIFICATE OF CORRECTION

PATENT NO.    : 5,654,171
DATED         : August 5, 1997
INVENTOR(S)   : SUGINAKA et al It is certified that error appears in the above-indentified patent and that said Letters Patent is hereby corrected as shown below:

Title page, Item [22], delete "Filed December 5, 1994" and insert
   --PCT Filed: September 5, 1990--.

Title page, before "Related U.S. Application Data" add the following:
   --[86]    PCT No.:      PCT/JP90/01135
             §371 Date:    June 12, 1991
             §102(e) Date: June 12, 1991

[87]    PCT Pub. No.: WO 91/03490
             PCT Pub. Date: March 21, 1991--

Signed and Sealed this

Eighth Day of June, 1999

Attest:

Q. TODD DICKINSON

Attesting Officer    Acting Commissioner of Patents and Trademarks